US009508936B2

(12) United States Patent
Melucci et al.

(10) Patent No.: US 9,508,936 B2
(45) Date of Patent: Nov. 29, 2016

(54) ORGANIC SEMICONDUCTOR MATERIAL

(71) Applicant: E.T.C. S.R.L., Bologna BO (IT)

(72) Inventors: Manuela Melucci, Bologna BO (IT); Laura Favaretto, Ozzano nell'Emilia BO (IT); Massimo Zambianchi, Cesena FC (IT); Raffaella Capelli, Bologna BO (IT); Michele Muccini, Bologna BO (IT)

(73) Assignee: E.T.C. S.R.L., Bologna (BO) (IT)

( * ) Notice: Subject to any disclaimer, the term of this patent is extended or adjusted under 35 U.S.C. 154(b) by 0 days.

(21) Appl. No.: 14/423,074

(22) PCT Filed: Oct. 8, 2013

(86) PCT No.: PCT/IB2013/059200
§ 371 (c)(1),
(2) Date: Feb. 20, 2015

(87) PCT Pub. No.: WO2014/057422
PCT Pub. Date: Apr. 17, 2014

(65) Prior Publication Data
US 2015/0214488 A1   Jul. 30, 2015

(30) Foreign Application Priority Data

Oct. 9, 2012   (IT) .............................. MI2012A1691

(51) Int. Cl.
*H01L 51/00*   (2006.01)
*C07D 495/04*   (2006.01)
*H01L 51/05*   (2006.01)

(52) U.S. Cl.
CPC ......... *H01L 51/0071* (2013.01); *C07D 495/04* (2013.01); *H01L 51/0068* (2013.01); *H01L 51/0074* (2013.01); *H01L 51/0558* (2013.01)

(58) Field of Classification Search
None
See application file for complete search history.

(56) References Cited

U.S. PATENT DOCUMENTS

| 5,276,009 | A | 1/1994 | Muenster et al. |
| 2015/0214488 | A1 | 7/2015 | Melucci et al. |
| 2015/0287932 | A1 | 10/2015 | Zambianchi et al. |
| 2015/0311448 | A1 | 10/2015 | Melucci et al. |

FOREIGN PATENT DOCUMENTS

| DE | 1954550 | 7/1971 |
| EP | 0467206 | 1/1992 |
| FR | 2066727 | 8/1971 |
| JP | 2009099942 A | 5/2009 |
| WO | 2006094292 | 9/2006 |
| WO | 2008127029 | 10/2008 |
| WO | 2010/131764 A1 | 11/2010 |

OTHER PUBLICATIONS

Facchetti, A. et al. "n-Type Buliding Blocks for Organic Electronics: A Homologous Family of Fourocarbon-Substitute Thiophene Oligomers with High Carrier Mobility" Advanced Materials; vol. 15, No. 1; Jan. 3, 2003, pp. 33-38.
Melucci, M. et al., "Polyvinyl-Locked versus Free Quaterthiophene: Effect of Spacital Contraints on the Electronic Properties of n-Hexylquaterthiophene" Chem.Phys. Chem. vol. 8; 2007, pp. 2621-2626.
Muccini, M. "A bright future for organic field-effect transistors", Nature Materials, vol. 5, No. 8, 1 (2006), pp. 605-613.
PCT International Search Report for PCT Application PCT/IB2012/052503 filed on May 18, 2012 in the name of E.T.C. S.R.L. Mail Date: Jul. 5, 2012. 4 pages.
Written Opinion for PCT/IB2012/052503 filed May 18, 2012 on behalf of E.T.C. S.R.L. Mail Date: Jul. 5, 2012. 6 pages.
International Preliminary Report on Patentability for PCT/IB2012/052503 filed May 18, 2012 on behalf of E.T.C. S.R.L. Mail Date: May 24, 2013. 22 pages.
International Search Report for PCT/IB2013/060128 filed on Nov. 14, 2013 in the name of E.T.C. S.R.L. Mail Date: Jan. 7, 2014. 4 pages.
Written Opinion of the International Searching Authority for PCT/IB2013/060128 filed on Nov. 14, 2013 in the name of E.T.C. S.R.L. Mail Date: Jan. 7, 2014. 6 pages.
Written Opinion of the International Preliminary Examining Authority for PCT/IB2013/060128 filed on Nov. 14, 2013 in the name of E.T.C. S.R.L. Mail Date: Nov. 3, 2014. 6 pages.
International Preliminary Report on Patentability for PCT/IB2013/060128 filed on Nov. 14, 2013 in the name of E.T.C. S.R.L. Mail Date: Jan. 23, 2015. 21 pages.
PCT International Search Report for PCT/IB2013/060162 filed on Nov. 15, 2013 in the name of E.T.C. S.R.L. Mail Date: Jan. 29, 2014. 4 pages.
PCT Written Opinion for PCT/IB2013/060162 filed on Nov. 15, 2013 in the name of E.T.C. S.R.L. Mail Date: Jan. 29, 2014. 5 pages.
Non-Final Office Action for U.S. Appl. No. 14/435,411, filed Apr. 13, 2015 in the name of Manuela Melucci. Mail Date: Jan. 13, 2016. 34 pages.
Final Office Action for U.S. Appl. No. 14/435,411, filed Apr. 13, 2015 in the name of Manuela Melucci. Mail Date: Jun. 24, 2016. 12 pages.
Restriction Requirement for U.S. Appl. No. 14/436,856, filed Apr. 17, 2015 in the name of Massimo Zambianchi. Mail Date: Dec. 3, 2015. 8 pages.
Non-Final Office Action for U.S. Appl. No. 14/436,856, filed Apr. 17, 2015 in the name of Massimo Zambianchi. Mail Date: Apr. 5, 2016. 30 pages.
Notice of Allowance for U.S. Appl. No. 14/436,856, filed Apr. 17, 2015 in the name of Massimo Zambianchi. Mail Date: Jul. 5, 2016. 23 pages.
Non-Final Office Action for U.S. Appl. No. 14/114,892, filed Mar. 25, 2014 in the name of Manuela Melucci. Mail Date: Jun. 17, 2014. 13 pages.

(Continued)

*Primary Examiner* — Alicia L Otton
(74) *Attorney, Agent, or Firm* — Steinfl & Bruno, LLP

(57) ABSTRACT

A novel compound useful as organic semiconductor material, and semiconductor devices containing such organic semiconductor material are described.

13 Claims, 4 Drawing Sheets

(56) References Cited

OTHER PUBLICATIONS

Non-Final Office Action for U.S. Appl. No. 14/570,777, filed Dec. 15, 2014 in the name of Manuela Melucci. Mail Date: Aug. 10, 2015. 12 pages.

Final Office Action for U.S. Appl. No. 14/570,777, filed Dec. 15, 2014 in the name of Manuela Melucci. Mail Date: Jan. 29, 2016. 11 pages.

PCT International Search Report mailed on Aug. 21, 2012 for PCT/IB2013/059200 filed on Oct. 8, 2013 in the name of E.T.C. S.R.L.

PCT Written Opinion mailed on Aug. 21, 2012 for PCT/IB2013/059200 filed on Oct. 8, 2013 in the name of E.T.C. S.R.L.

Bijleveld, Johan C. et al. "Poly(diketopyrrolopyrrole-terthiophene) for Ambipolar Logic and Photovoltaics" J.Am.Chem.Soc. (2009), 131, pp. 16616-16617.

Sonar, Prashant. et al "A Low-Bandgap Diketopyrrolopyrrole-Benzothiadiazole-Based Copolymer for High-Mobility Ambipolar Organic Thin-Film Transistors" Mater. (2010), 22, 47, pp. 5409-5413.

Yoon, Myung-Han et al. "Organic Thin-Film Transistors Based on Carbonyl-Functionalized Quaterthiophenes: High Mobility N-Channel Semiconductors and Ambipolar" Transport J. Am. Chem. Soc.( 2005), 127, pp. 1348-1349.

Facchetti, Antonio et al. "Building Blocks for n-Type Organic Electronics: Regiochemically Modulated Inversion of Majority Carrier Sign in Perfluoroarene-Modified Polythiophene Semiconductors" Angew. Chem. Int. Ed. (2003), 42, pp. 3900-3903.

Letizia, Joseph A. et al. "n-Channel Polymers by Design: Optimizing the Interplay of Solubilizing Substituents, Crystal Packing, and Field-Effect Transistor Characteristics in Polymeric Bithiophene-Imide Semiconductors" J. Am. Chem. Soc. (2008), 130, pp. 9679-9694.

Zhang, Qing T. et al. Alternating Donor/Acceptor Repeat Units in Polythiophenes.Intramolecular Charge Transfer for Reducing Band Gaps in Fully Substituted Conjugated PolymersJ.Am.Chem.Soc. (1998) 120, 5355-5362.

Pomerantz, Martin "Planar 2,2-bithiophenes with 3,3- and 3,3,4,4-substituents. A computational study" Tetrahedron Letters 44 (2003) pp. 1653-1565.

Nielsen, Christian B. "New Regiosymmetrical Dioxopyrroloand Dihydropyrrolo-Functionalized Polythiophenes" Organic Letters (2004), 6, 19, 3381-3384.

Wei Hong et al, "Linear fused dithieno [2,3-b: 3 '2'-d]thiophene diimides" Organic Letters, vol. 13, No. 6 (2011), pp. 1410-1413.

Ronova, Iga A et al: "The effect of conformational rigidity on the initial decomposition temperature of some heterocyclic polyimides", High Performance Polymers, Institute of Physics Publishing, Bristol GB, vol. 14, No. 2 (2002) pp. 195-208.

Gaina C. et al, "Polyimides containing 1,4-dithiine units and their corresponding thiophene 2,3,4,5 tetracarboxylimide units" High Performance Polymers, Institute of physics publishing, Bristol GB, vol. 11, No. 2 (1999) pp. 185-195.

Melucci, Manuela et al: 11 Thienopyrrolyl 1-15 di one end-capped oligothiophene ambipolar semiconductors for thin film- and light emitting transistors 11 , Chemical Communications, vol. 47, No. 43, Nov. 21, 2011 pp. 11840-11842.

ORGANIC SEMICONDUCTOR MATERIAL

CROSS REFERENCE TO RELATED APPLICATIONS

The present application is the US national stage of International Patent Application PCT/IB2013/059200 filed internationally on Oct. 8, 2013 which, in turn, claims priority to Italian Patent Application No. MI2012A001691 filed on Oct. 9, 2012.

The present invention relates to a novel n-type organic semiconductor material, and semiconductor devices containing said n-type organic semiconductor material.

It is known that organic semiconductors are materials into which charge can be reversibly introduced by the application of electromagnetic energy or chemical dopants. The electronic conductivity of these materials lies between that of metals and insulators, spanning a broad range of $10^{-9}$ to $10^{3}$ $\Omega^{-1}$ $cm^{-1}$. As in traditional inorganic semiconductors, organic materials can function either as p-type or n-type. In p-type semiconductors the majority carriers are holes, while in n-type the majority carriers are electrons.

The vast majority of the prior art has focused on the design, synthesis, and structure-property relationships of p-type organic semiconductor materials, including: oligoacenes, fused oligothiophenes, anthradithiophenes, carbazoles, oligophenylenes, and oligofluorenes, some of which have resulted in field-effect transistors with performance superior to amorphous silicon. In contrast, the development of n-type oligomer and polymer semiconductors has lagged behind p-type materials. In fact, compared to the p-type semiconductors, n-type semiconductors are still not fully developed, and the performances are not satisfactory.

Organic semiconductors that possess a high electron affinity are however also required, as both p- and n-channel materials are required for efficient logic circuits and organic solar cells. Indeed, n-type organic field-effect transistors are envisioned as key components of organic p-n junctions, bipolar transistors, and complementary integrated circuits leading to flexible, large-area, and low-cost electronic applications.

A variety of organic semiconductors have been considered in the art as n-type organic semiconductor materials.

Aromatic tetracarboxylic anhydride and their diimide derivatives were reported among the first n-channel materials. Among the materials of this class, perylenetetracarboxylic diimides having fluorinated side chains showed mobilities up to 0.72 $cm^2V^{-1}$ $s^{-1}$, which only slightly decreased upon air exposure. Air stability, packing grain size and morphology of the deposited films as well as electrical performance can be altered by varying side-chain length, insertion of oxygenated groups and degree of fluorination. However, most of the perylene building blocks, due to the structural rigidity and moderate solubility, do not allow readily structural changes limiting the volume of materials accessible.

Other classes of n-type organic materials have been described such as cyanovinyl oligomers, fullerenes.

J. Am. Chem. Soc. 2009, 131, 16616-16617 describes ambipolar charge transport properties of diketopyrrolopyrrole-copolymers.

A benzothiadiazole-diketopyrrolopyrrole copolymer described in Mater. 2010, 22, 47, 5409-5413, shows high and balanced hole- and electron mobilities of 0.35 $cm^2V^{-1}s^{-1}$ and 0.40 $cm^2V^{-1}s^{-1}$, respectively. Larger electron mobilities values up to 0.85 $cm^2V^{-1}s^{-1}$ were achieved in air for electron-only transporting n-type polymer, called poly {[N,N9-bis(2-octyldodecyl)-naphthalene-1,4,5,8-bis(dicarboximide)-2,6-diyl]-alt-5,59-(2,29-bithiophene)}, (Polyera Activink N2200), in a staggered top gate configuration.

N-type semiconductor materials consisting of oligothiophenes bearing fluorinated side groups have been also described in J. Am. Chem. Soc. 2005, 127, 1348 and Angew. Chem. Int. Ed. 2003, 42, 3900. These oligomers showed mobilities up to 0.43 $cm^2V^{-1}s^{-1}$. However, OFETs based on most of these perfluoroaryl and perfluoroalkylaryl substituted materials were unstable in air or suffered from high threshold voltage. Fluorocarbonyl-functionalized oligomers were also described, which showed improved air stability, but lower electron mobilities with respect to fluorinated oligomers.

Oligomers and polymers containing a bithiophene-imide units as inner core have also been described.

For example, J. Am. Chem. Soc. 2008, 130, 9679-9694 describes N-alkyl-2,2'-bithiophene-3,3'-dicarboximide-based homopolymers and copolymers showing p-type or n-type semiconductor behavior depending on the polymeric structure. However, no air-stable devices could be achieved with such materials. In addition, the poor reactivity of the starting dihalogenated bithiophene-imide compounds limits the accessibility of this class of materials.

J. Am. Chem. Soc. 1998, 120, 5355-5362, Tetrahedron Letters 44 (2003)1653-1565 disclose copolymers containing electron poor 3,4-imido-thienyl blocks alternated to electron rich amino substituted thienyl blocks. No investigation was performed regarding the electrical properties of such copolymers.

N-alkylated poly(dioxopirrolothiophene)s are described in Organic Letters 2004, 6, 19, 3381-3384. However, no proof of an efficient n-type behavior in OFET devices is reported.

Each of the afore mentioned class of materials has poor electrical performances.

WO2008/127029 relates to dioxypirrolo-heterocyclic compounds having the pyrrole moiety fused to the 3,4 position of the thienyl ring and organic electronic devices using said dioxypirrolo-heterocyclic compounds.

Wei Hong et al, "Linear fused dithieno [2,3-b: 3'2'-d] thiophene diimides" Organic Letters, vol 13, no. 6, 18 Mar. 2011, pages 1410-1413, discloses a class of linear fully fused dithieno thiophene diimides.

The documents: DE1954550; Ronova Iga A et al: "The effect of conformational rigidity on the initial decomposition temperature of some heterocyclic polyimides", High Performance Polymers, Institute of Physics Publishing, Bristol GB, vol. 14, No. 2, 1 Jan. 2002, pages 195-208; and Gaina C. et al, "Polyimides containing 1,4-dithiine units and their corresponding thiophene 2,3,4,5 tetracarboxylimide units" High Performance Polymers, Institute of physics publishing, Bristol GB, vol. 11, No. 2, 1 Jun. 1999, pages 185-195, disclose polymeric diimide compounds in which the member connecting the polymer repeating units is the N-imidic substituent. The three last cited documents do not mention any semiconductor property of the compounds therein disclosed.

WO2006/094292 discloses thienopyridine compounds capable of modulating the stability and/or activity of hypoxia inducible factor, pharmaceutical compositions comprising said compounds and chemical intermediates useful for preparing said compounds. Among said chemical intermediates, specific compounds having a 4,6-dioxo-thieno[2,3-c]pyrrole nucleus are disclosed.

EP0467206 discloses specific compounds having a 4,6-dioxo-thieno[2,3-c]pyrrole nucleus and their use as herbicide.

However, WO2006/094292 and EP0467206 do not teach the semiconductor properties of said compounds.

Therefore, there is still the need of n-type organic semiconductor materials or compounds that possess higher electron mobility properties.

In the present specification and in the claims, the term "n-type organic semiconductor" means a material that, inserted as active layer in a field effect device architecture with a source, a drain and gate control electrodes, shows an electron mobility higher than $10^{-7}$ cm$^2$V$^{-1}$s$^{-1}$.

It is an object of the present invention to provide new organic materials suitable for use as semiconductor material which is free from said disadvantages. Said object is achieved with compounds whose main features are disclosed in the first claim, a use of said compound whose main features are disclosed in claim 11 and an electronic device whose main features are disclosed in claim 13. Other features of said compound are disclosed in claims 2 to 10.

Advantageously, the compounds according to the present invention may be useful as p-type, n-type or ambipolar organic semiconductor material.

Particularly, the compounds according to the present invention possess high electron mobility properties, excellent stability under atmospheric conditions and are accessible through synthetically easy processes.

Further advantages and features of the compounds, materials and devices according to the present invention will become clear to those skilled in the art from the following detailed and non-limiting description of an aspect thereof with reference to the attached drawings, wherein.

Figure 1:
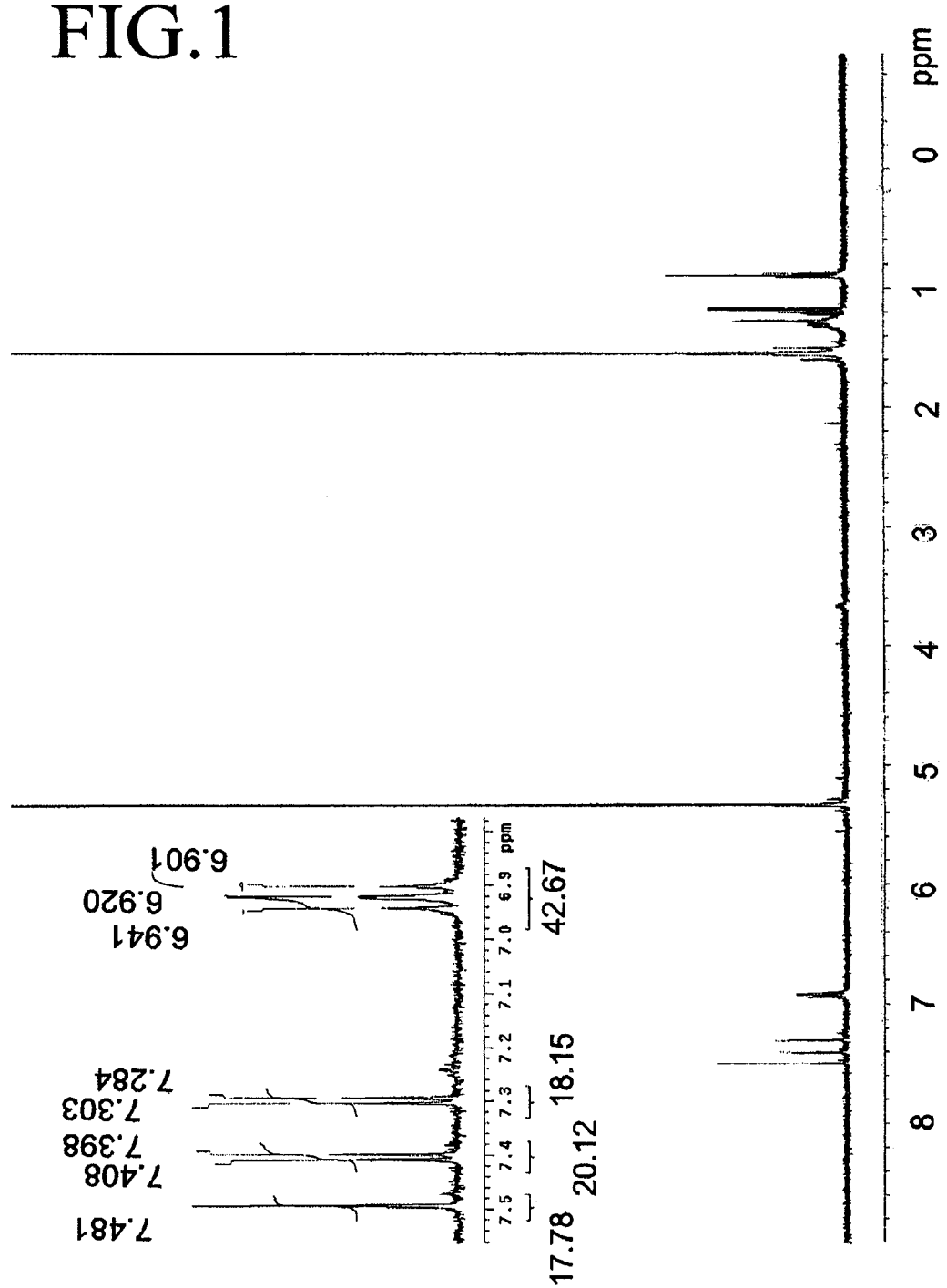
FIG. 1 shows the $^1$H-NMR spectrum of a preferred compound 5 according to the present invention.
Figure 2:
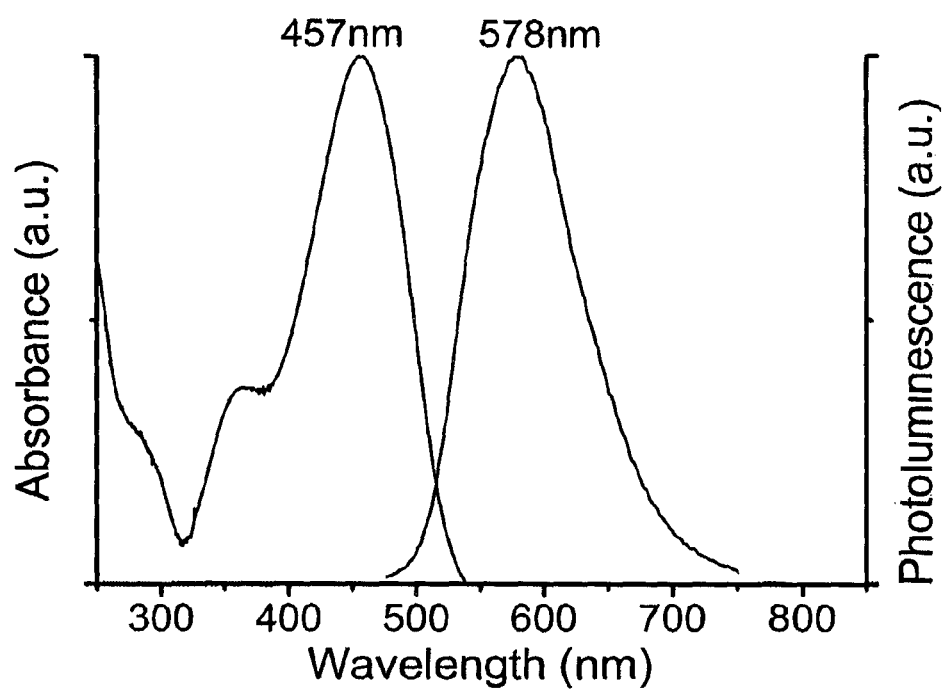
FIG. 2 shows UV-vis and PL spectra of a compound 5 according to the present invention.
Figure 3:
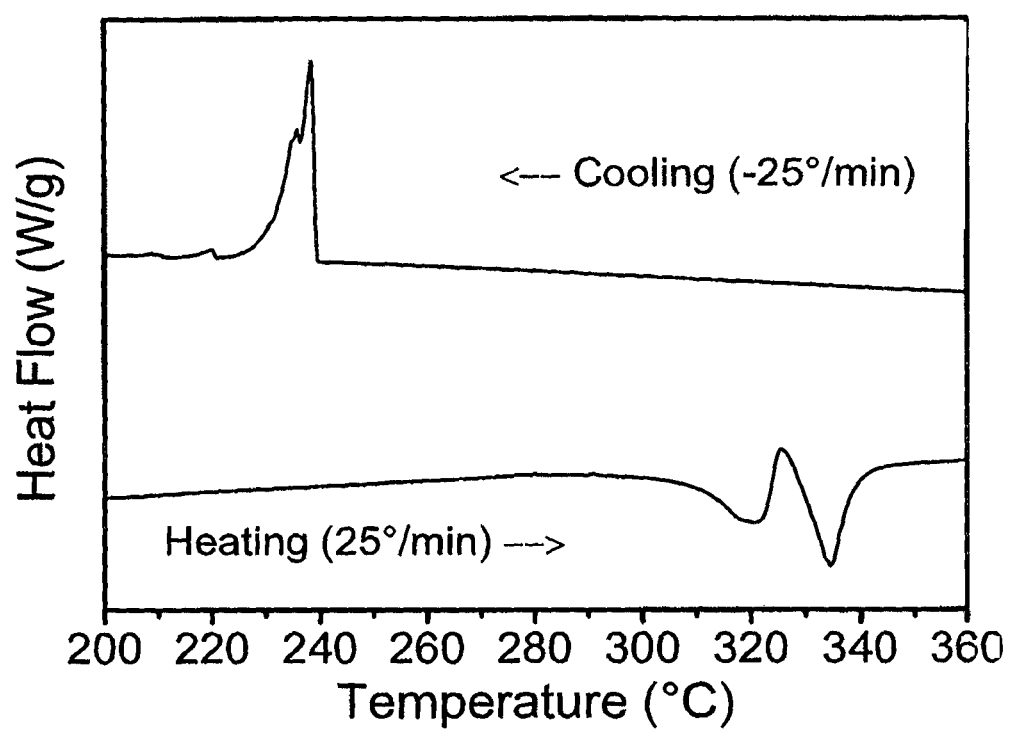
FIG. 3 shows a differential scanning calorimetry (DSC) spectrum of a preferred compound 5 according to the present invention.

According to an aspect of the present invention, a compound of formula (I) or (II) or (III) or (IV) is provided:

formula (I)

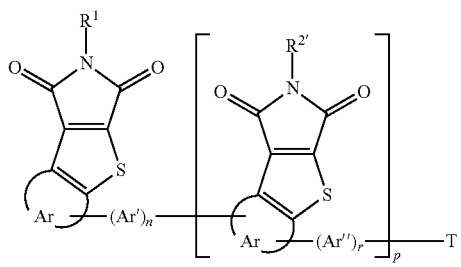

formula (II)

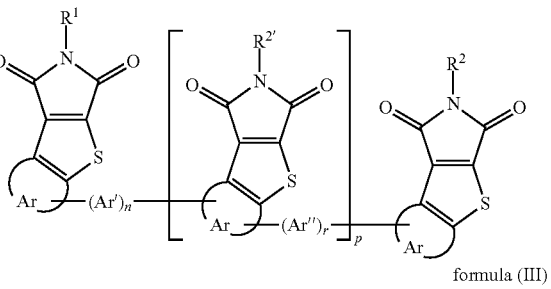

formula (III)

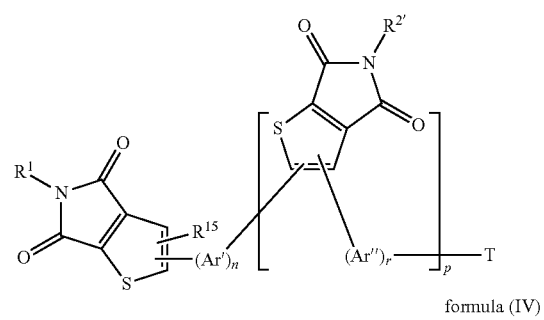

formula (IV)

wherein:
R$^1$, R$^2$, R$^{2'}$ independently of each other, are selected in the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers;

Ar is selected in the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers;

Ar', Ar'', independently of each other, are moieties selected in the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers;

R$^{15}$ is selected in the group consisting of hydrogen, halogen, C$_1$-C$_{20}$ linear or branched alkyl groups, C$_1$-C$_{20}$ linear or branched heteroalkyl groups, C$_1$-C$_{20}$ linear or branched heteroalkoxyalkyl groups, C$_1$-C$_{20}$ linear or branched halogenoalkyl groups, C$_3$-C$_{20}$ linear or branched cycloalkyl groups, C$_1$-C$_{20}$ linear or branched hydroxyalkyl groups, $C_1$-$C_{20}$ linear or branched alkoxyl groups and $C_1$-$C_{20}$ linear or branched nitrile groups;

n, r, independently of each other, are integers between 1 and 50;

p is an integer between 0 and 5; and

T is a terminal unit of the compound and is selected among hydrogen, $C_1$-$C_{40}$ linear or branched alkyl groups, $C_1$-$C_{40}$ linear or branched haloalkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched heteroalkoxyalkyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups, monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers;

with the exception of compounds of formula A:

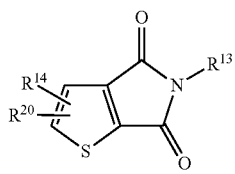

formula A wherein $R^{13}$ is selected in the group consisting of phenyl, 4-chlorophenyl, 3-trifluoromethylphenyl; $R^{14}$ is selected in the group consisting of phenyl, 2-fluorphenyl, 3-fluorphenyl, 4-fluorphenyl, 2-chlorphenyl, 3-chlorphenyl, 4-chlorphenyl, 2-methylphenyl, 3-methylphenyl, 4-methylphenyl, 2-trifluoromethylphenyl, 3-trifluormethylphenyl, 4-trifluormethylphenyl, 2-methoxyphenyl, 3-methoxyphenyl, 4-methoxyphenyl, 2,4-dichlorphenyl, 2,4,6-trimethylphenyl, 2-thienyl, 3-thienyl, 2-pyridyl, 3-pyridyl, 4-pyridyl; and $R^{20}$ is selected in the group consisting of H, Cl, F, methyl, methoxy.

The value of p is preferably 0, 1 or 2.

The values of n and r, independently on each other, are preferably comprised between 2 and 50, more preferably between 2 and 30, even more preferably between 2 and 10.

When p assumes the values of 0, then n is particularly preferably comprised between 2 and 50, more preferably between 2 and 30, even more preferably between 2 and 10.

Preferably, $R^{15}$ is hydrogen.

$R^1$, $R^2$ and $R^{2'}$ are preferably $C_6$-$C_{50}$ monocyclic aryl groups, $C_{10}$-$C_{50}$ polycyclic aryl groups, $C_1$-$C_{50}$ monocyclic heteroaryl groups, $C_6$-$C_{50}$ polycyclic heteroaryl groups and benzyl groups, that may be substituted. Preferably, $R^1$, $R^2$ and $R^{2'}$ are selected in the group consisting of phenyl group, substituted phenyl groups, benzyl groups and substituted benzyl groups.

The preferred substituents of said monocyclic aryl groups, polycyclic aryl groups, monocyclic heteroaryl groups, polycyclic heteroaryl groups and benzyl groups of $R^1$, $R^2$ and $R^{2'}$ are selected among halogens, alkenyl, alkynyl or heteroalkyl groups. More preferably, said substituent groups are selected in the group consisting of $C_1$-$C_{12}$ alkyl, $C_1$-$C_{12}$ perfluoroalkyl, $C_1$-$C_{12}$ oxyalkyl, $C_1$-$C_{12}$ aminoalkyl, $C_1$-$C_{12}$ tioalkyl, $C_1$-$C_{12}$ haloalkyl, $C_1$-$C_{12}$ carboxyalkyl groups, $C_1$-$C_{12}$ silicioalkyl and $C_3$-$C_{12}$ branched alkyl-alkenyl and $C_3$-$C_{12}$ alkyl-alkynyl groups.

Even more preferably, $R^1$, $R^2$ and $R^{2'}$ are selected in the group consisting of phenyl group, alkyl substituted phenyl groups, halophenyl groups.

Preferably, Ar, Ar' and Ar'', independently of each other, are selected in the group consisting of $C_6$-$C_{50}$ monocyclic aryl groups, $C_6$-$C_{50}$ substituted monocyclic aryl groups, $C_{10}$-$C_{50}$ polycyclic aryl groups, $C_{10}$-$C_{50}$ substituted polycyclic aryl groups, monocyclic $C_1$-$C_{50}$ heteroaryl groups, $C_1$-$C_{50}$ substituted monocyclic heteroaryl groups, $C_6$-$C_{50}$ polycyclic heteroaryl groups, $C_6$-$C_{50}$ substituted polycyclic heteroaryl groups.

According to an aspect of the present invention, the compounds of following formulas (Ia), (IIa), (IIIa) and (IVa) are provided, which correspond to those of formulas (I), (II), (III), (IV) wherein p is equal to 0 and $R^{15}$ is hydrogen:

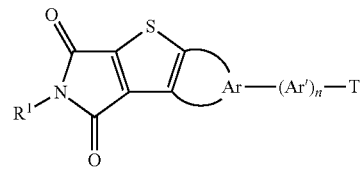

formula (Ia)

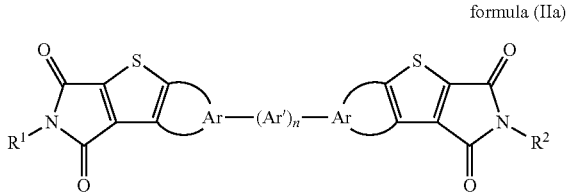

formula (IIa)

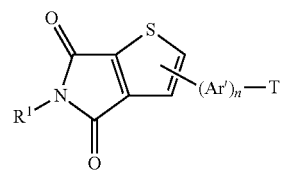

formula (IIIa)

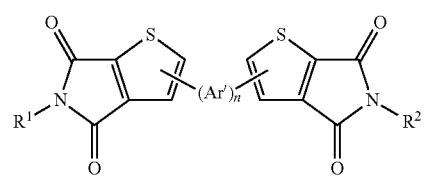

formula (IVa)

wherein $R^1$, $R^2$, Ar, Ar', T and n are as above defined.

In the present description and in the claims, the curved lines in formulas (I), (Ia), (II) and (IIa), connecting the Ar moiety to the thieno(bis)imide unit, indicate that said Ar moiety forms a fused ring system with said thieno(bis)imide unit.

In addition, as usual in chemical drawing practice, in the present description and in the claims the bond lines crossing the thiophene double bond in formulas (III), (IIIa), (IV) and (IVa) indicates that the $(Ar')_n$ moiety may be bound to any of the 2 or 3 position in the thiophene ring and is not fused thereto. Preferably, the $(Ar')_n$ moiety is bound to the 2 position of the thiophene ring.

In formulas (Ia), (IIa), (IIIa) and (IVa) the integer n is preferably comprised between 1 and 30, more preferably between 2 and 30, even more preferably between 2 and 10.

The compounds according to the invention wherein n is 2 are characterized by an advantageously high solubility in a number of solvents, for example dichloromethane, dimethyl sulfoxide, tetrahydrofuran.

In formulas (I), (Ia), (II) and (IIa), the (Ar')$_n$ moiety may be bound to any position of the Ar moiety that is fused to the thieno(bis)imide unit.

Preferably, the Ar' is a unit selected among the following groups (a), (b), (c), (d), (e), (f), (g), (h), (i), (l), (m), (n), (o), (p), (q), (r):

(a)
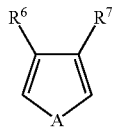

(b)
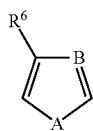

(c)
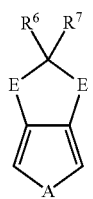

(d)
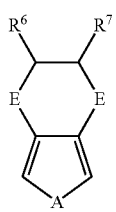

(e)
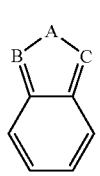

(f)
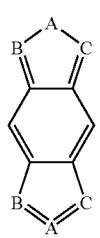

(g)
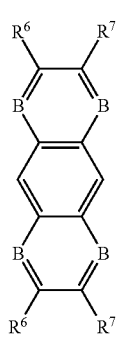

-continued (h)
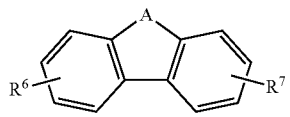

(i)
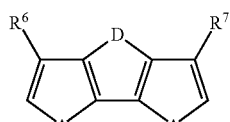

(l)
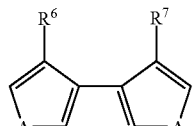

(m)
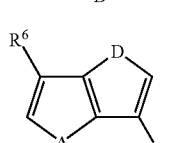

(n)
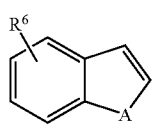

(o)
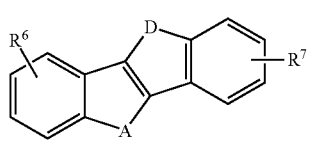

(p)
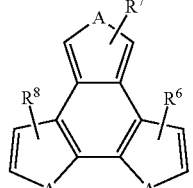

(q)
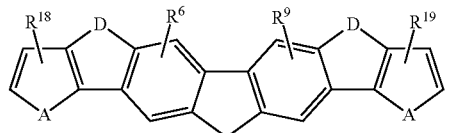

(r)
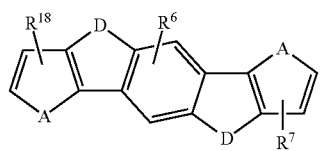

wherein A is selected in the group consisting of S, O Se, atoms and SO, SO$_2$, R$^{17}$—P=O, P—(R$^{17}$)$_2$, N—R$^{16}$, Si(R$^{16}$)$_2$ groups;

D is selected in the group consisting of C, S, O Se, atoms and SO, SO$_2$, R$^{17}$—P=O, P—(R$^{17}$)$_2$, N—R$^{16}$, Si(R$^{16}$)$_2$ groups;

B, C, independently of each other, are selected in the group consisting of C, N atoms and NR$^{16}$ group;

E is selected in the group consisting of C(R$^{16}$)$_2$, S, O, and NR$^{16}$ group;

R$^6$, R$^7$, R$^8$, R$^9$, R$^{18}$ and R$^{19}$, independently of each other, are selected in the group consisting of hydrogen, halogens, C$_1$-C$_{20}$ linear or branched alkyl groups, C$_2$-C$_{20}$ linear or branched alkenyl groups, C$_3$-C$_{20}$ linear or branched alkyl-alkenyl groups, C$_1$-C$_{20}$ linear or branched halogenoalkyl groups, C$_2$-C$_{20}$ linear or branched alkynyl groups, C$_3$-C$_{20}$ linear or branched alkyl-alkynyl groups, C$_3$-C$_{20}$ linear or branched cycloalkyl groups, C$_1$-C$_{20}$ linear or branched hydroxyalkyl groups, C$_1$-C$_{20}$ linear or branched alkoxyl groups, C$_1$-C$_{20}$ linear or branched heteroalkoxyalkyl groups, C$_1$-C$_{20}$ linear or branched alkylcarboxylic groups, C$_1$-C$_{20}$ linear or branched alkylcarboxyamide groups, C$_1$-C$_{20}$ linear or branched alkylsulphonic groups, C$_1$-C$_{20}$ linear or branched nitrile groups, C$_5$-C$_{40}$ aryl groups, C$_6$-C$_{40}$ alkylaryl groups (OK);

R$^{16}$, R$^{17}$ independently of each other, are selected in the group consisting of hydrogen, C$_1$-C$_{20}$ linear or branched alkyl groups, C$_2$-C$_{20}$ linear or branched alkenyl groups, C$_3$-C$_{20}$ linear or branched alkyl-alkenyl groups, C$_1$-C$_{20}$ linear or branched halogenoalkyl groups, C$_2$-C$_{20}$ linear or branched alkynyl groups, C$_3$-C$_{20}$ linear or branched alkyl-alkynyl groups, C$_3$-C$_{20}$ linear or branched cycloalkyl groups, C$_1$-C$_{20}$ linear or branched hydroxyalkyl groups, C$_1$-C$_{20}$ linear or branched alkoxyl groups, C$_1$-C$_{20}$ linear or branched heteroalkoxyalkyl groups, C$_1$-C$_{20}$ linear or branched alkylcarboxylic groups, C$_1$-C$_{20}$ linear or branched alkylcarboxyamide groups, C$_1$-C$_{20}$ linear or branched alkylsulphonic groups, C$_1$-C$_{20}$ linear or branched nitrile groups, C$_5$-C$_{40}$ aryl groups, C$_6$-C$_{40}$ alkylaryl groups.

In formulas (e) and (n), it is meant that the substituent group may be bound to any C— position of any ring forming the delocalized system.

Examples of the above described groups of formula (a)-(r) are for example the following:

(b1)

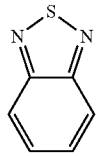
(e1)

(f1)

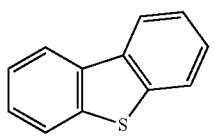
(h1)

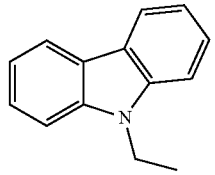
(h1)

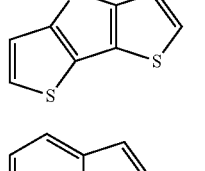
(i1)

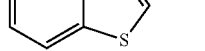
(n1)

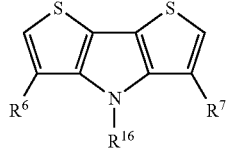
(i2)

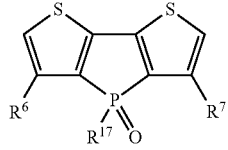
(i3)

In other preferred embodiments of the present invention, the Ar' moiety may be a dimer comprising a thiophene or phenyl unit that is linked to another aryl unit such as the above represented (a)-(r) groups, like in the following formulas (s) and (t):

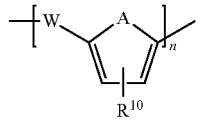
(s)

(t)

wherein W is a moiety selected in the group consisting of the above indicated groups (a) to (r), and R$^{10}$ is a moiety selected in the same group as R$^6$-R$^9$.

More preferably, the Ar' group may be a dimer comprising a thiophene unit that is α-linked to a polycyclic condensed thiophene unit such as in the following (Ar')$_n$ moieties of formula (u) and (v):

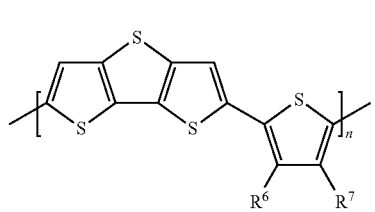
(u)

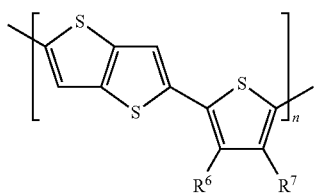
(v)

wherein $R^6$, $R^7$ and n have the above described meanings.

In an embodiment of the invention, Ar' is a thiophene unit or substituted thiophene unit, wherein the $(Ar')_n$ moiety is a linear chain of α-linked thiophene units or substituted thiophene units.

The Ar moiety fused to the thieno(bis)imide unit of the compounds of formulas (I), (Ia), (II), and (IIa) according to the present invention may be advantageously formed of one, two or three aromatic rings.

Preferably, in formulas (I), (Ia), (II), and (IIa), Ar is selected in the group consisting of the following rings (α), (β), (γ), (δ), (∈), (ζ), (η), (θ), (ι):

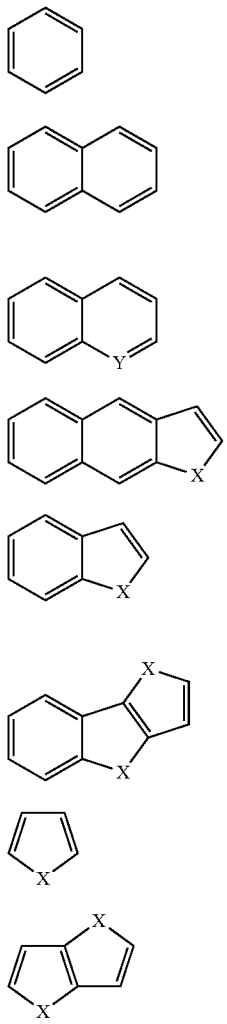

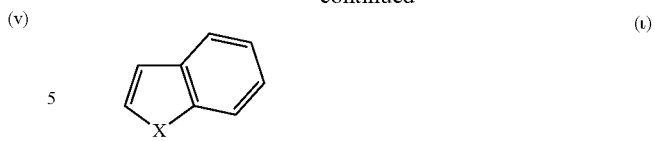
(ι)

wherein X is selected in the group consisting of S, SO, $SO_2$, O, Si, Se, $NR^3$, Y is selected in the group consisting of C and N;

$R^3$ is selected in the group consisting of hydrogen, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, $C_6$-$C_{40}$ alkylaryl groups.

Preferably, in formulas (II), (IIa), (IV) and (IVa), $R_1$ is the same as $R_2$.

According to a preferred aspect of the invention, a linear α-linked oligothiophene di-imide compound of formula (V) is provided:

formula (V)

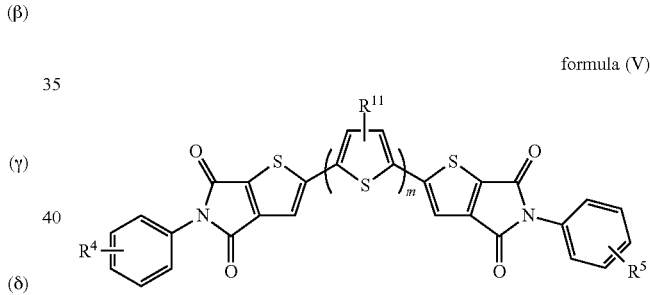

wherein $R^4$, $R^5$, $R^{11}$, independently of each other, are selected in the group the group consisting of hydrogen, halogens, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, $C_6$-$C_{40}$ alkylaryl groups; and m is an integer between 1 and 50.

More preferably, in compound of formula (V), m is comprised between 1 and 30, more preferably between 2 and 30, even more preferably, m is comprised between 2 and 10.

According to a preferred aspect of the invention, a compound is provided having formula (VI):

formula (VI)

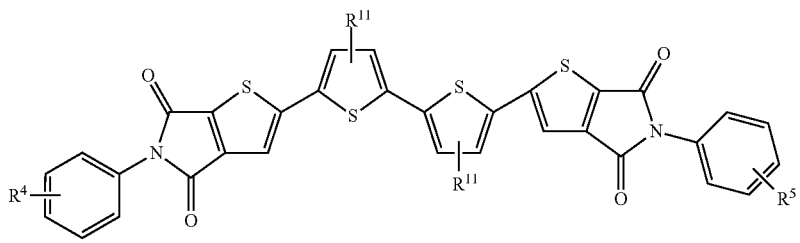

wherein $R^4$, $R^5$ and $R^{11}$ are as above defined with reference to formula (V).

According to another preferred aspect of the invention, a compound is provided having formula (VII):

formula (VII)

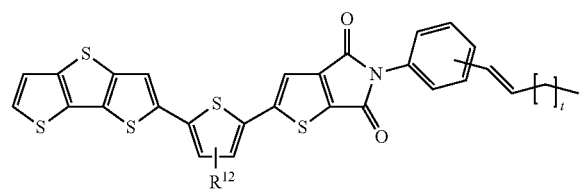

wherein $R^{12}$ has the same meaning of $R^{11}$ above defined with reference to formula (V) and t is an integer between 2 and 6.

As it may well be understood, the compound of formula (VII) derives from general formula (IIIa) wherein n is equal to 1; Ar' is a unit of formula (u) wherein $R^6$ is $R^{12}$, $R^1$ is a phenyl group substituted with an alkenyl group.

In the formulas (V), (VI), (VII) the symbols $R^4$, $R^5$, $R^{11}$ and $R^{12}$ are meant to indicate both a single and a multiple substitution of the phenyl and/or thiophene ring.

Preferably, in formula (VII) the alkenyl group is in the para position of the N-substituent phenyl group, such as in formula (VIIa):

formula (VIIa)

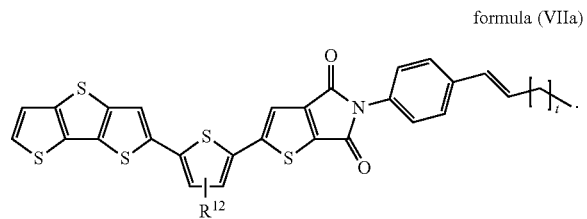

Without wishing to limit the present invention to any theory, it is believed that the imido-thiophene moiety allows for the combination of the strong electron-withdrawing effect of the carboxylic groups, which contributes in lowering the LUMO energy level of the final oligomer, to the chemical versatility, robustness and plasticity of the thienyl ring. This allows the realization of novel α-conjugated materials with high electron affinities comparable to the currently more performing n-type semiconducting organic materials.

Among the main advantages of such compounds with respect to other classes of n-type materials are to be mentioned the easy accessibility and structural versatility.

As a matter of fact, the imide moieties can be easily fused to the thienyl ring, as described below. The imido-thiophene moiety can easily be mono- or dihalogenated to realize linear or branched oligomers.

Finally N-substitution, particularly with arylic moieties can strongly influence the solid state packing and thin film morphology of π-conjugated thieno(bis)imide based materials.

It is believed that arylic pendants can promote close molecular packing through enhanced intermolecular π-π stacking interactions.

The solid-state morphology of conjugated oligomers and polymers plays an important role in the performance characteristics of electronic devices, e.g., organic solar cells (OPVDs), organic thin-film transistors (OTFTs) and organic light emitting transistors (OLETs). For example both exciton migration and carrier mobility, crucial parameter for charge transport based devices, are strongly modulated by the solid state packing of the conjugated backbones. In particular, increased intermolecular overlap of electronic wave functions leads to increased bandwidth, which is directly related to carrier mobility in the coherent transport regime.

The advantage of the compounds of formulas (I) and (II), wherein the imido-thiophene block is inserted into fused heterocycles with high degree of α-conjugation and planar structure, is that further tuning of the electronic levels as well as the morphology and optoelectronic properties of the final oligomers are possible.

The thiophene-imide moiety can be coupled to selected π-conjugated cores by cross-couplings under conventional or microwave-assisted methods as described below.

The easy accessibility of the compounds according to the invention also allows an easy modification of the oligomer size, and degree and type of molecular functionalization, which in turn permits to tailor the compounds properties as a function of the particular requirements of the desired application.

The compounds according to the present invention can be obtained with electronic level of purity by chromatography, crystallization and sublimation, with unambiguous molecular structure determination through classic analytical methods.

Contrarily to the thiophene-3,4-imide polymers, bithiophene-imide polymers and perylene tetracarboxylic diimide systems according to the prior art, this class of materials can be prepared with high reproducibility from batch to batch, which is crucial to achieve devices with reproducible responses. In addition, they can be adapted to solution processing by inserting tailored arylic groups as N-substituents.

Another advantage of the compounds according to the present invention consists in its high self-organization capability and order in thin films, due to their chemical structure comprising an imide moiety as alpha-end-substituent rather than beta inner substituent.

According to still another aspect of the invention, it is provided a process for the production of a compound according to the invention, wherein the process comprises reiterative halogenation of aromatic compounds and cross-coupling reactions.

The processes according to the present invention are preferably catalized by palladium.

The compounds according to the invention of formulas (I), (II), (III), and (IV) may be obtained starting from a dihalogenated aromatic halide, such as in the following Schemes 1 and 2:

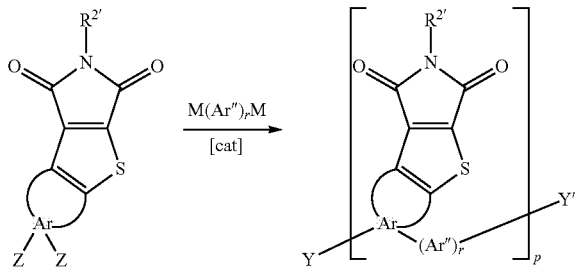
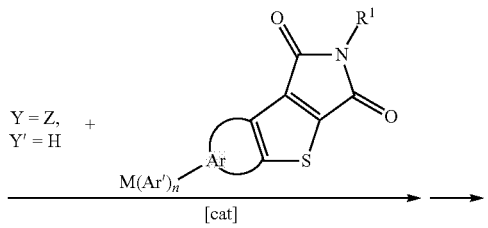
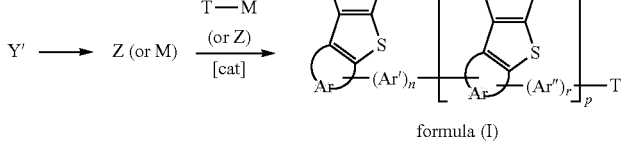
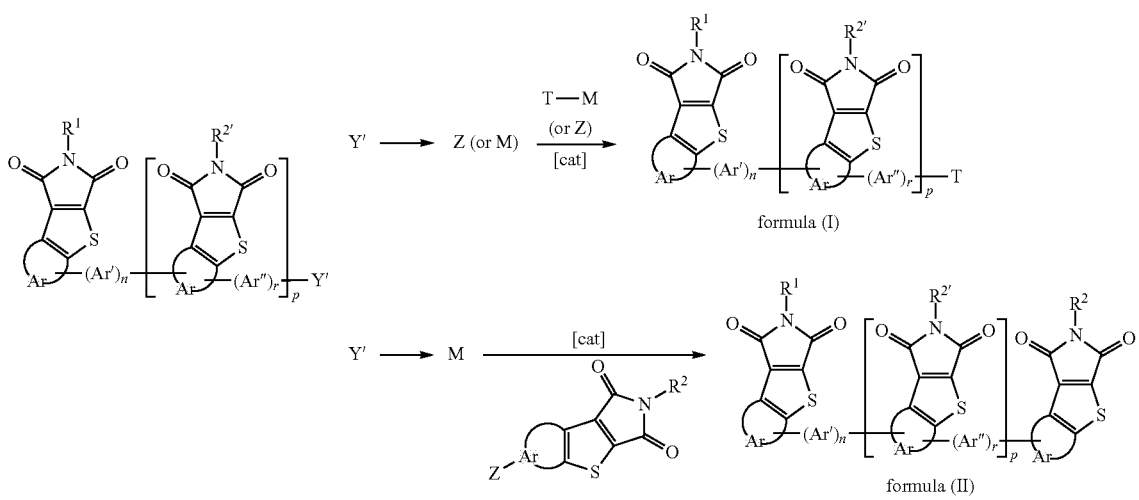
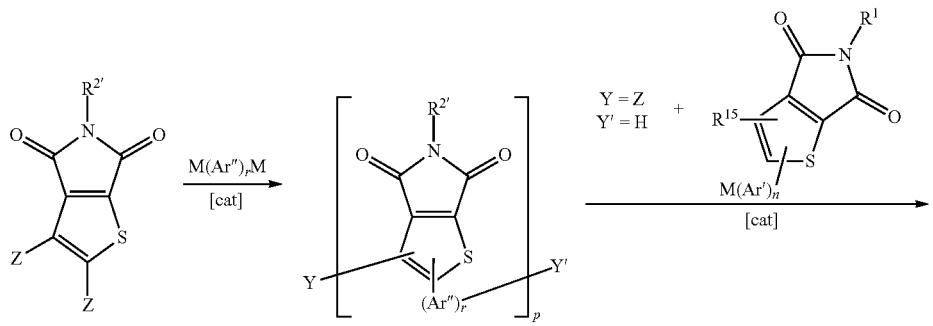

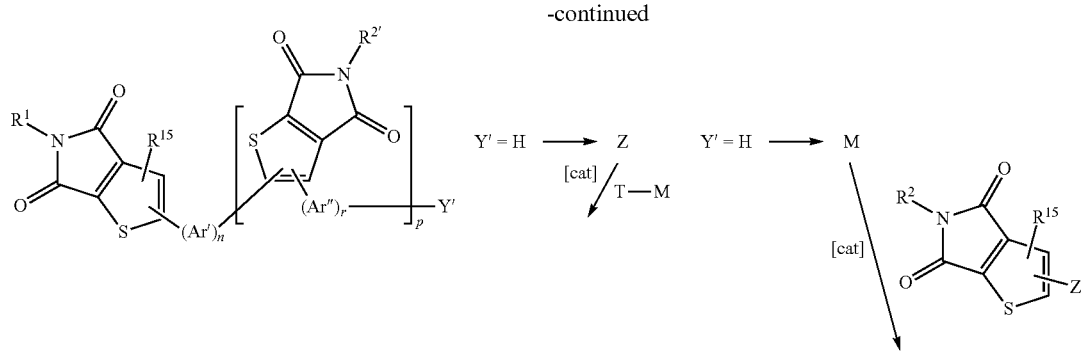

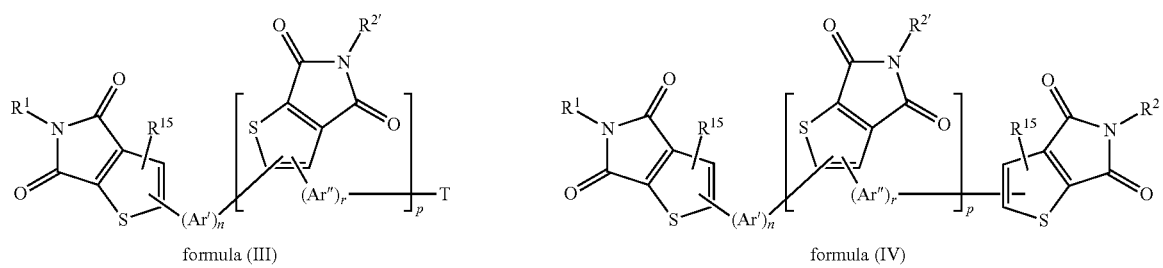

formula (III)          formula (IV)

wherein Z is selected among halogen atoms, such as Br, I; M is an organometal compound such as B(OR')$_2$ and SnR"$_3$ wherein R' is an hydrogen or an alkyl moiety and R" is an alkyl moieties; and [cat] is a palladium based catalyst.

According to an alternative synthetic process, direct arylation reaction could be used in place of conventional cross-coupling. In this case, no organometallic species (Ar-M) are required since this reaction typically involves a halogenated framework (Ar—Z) and an unsubstituted one (Ar'—H). As known in the art, direct arylation may be catalyzed by Palladium complexes.

Scheme 1a shows possible synthetic approaches for the preparation of the starting materials of the process of scheme 1, wherein Z is halogen and NZS means halogenated succinimide. Depending on the type of the fused heterocycle, pathway a or b should be selected.

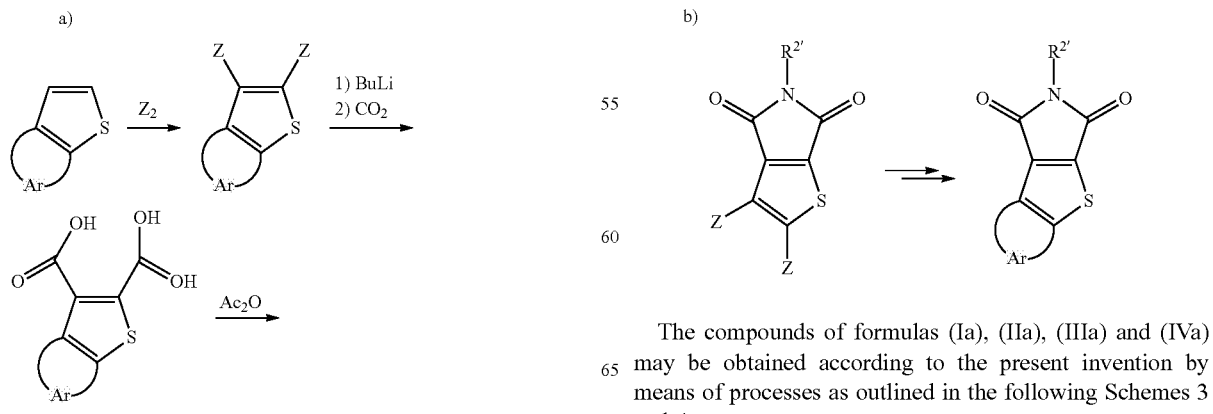

The compounds of formulas (Ia), (IIa), (IIIa) and (IVa) may be obtained according to the present invention by means of processes as outlined in the following Schemes 3 and 4:

Scheme 3

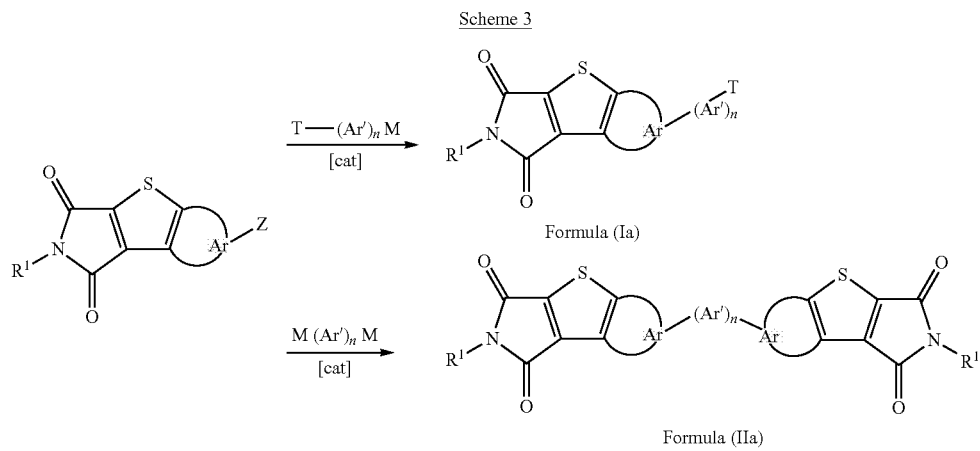

Scheme 4

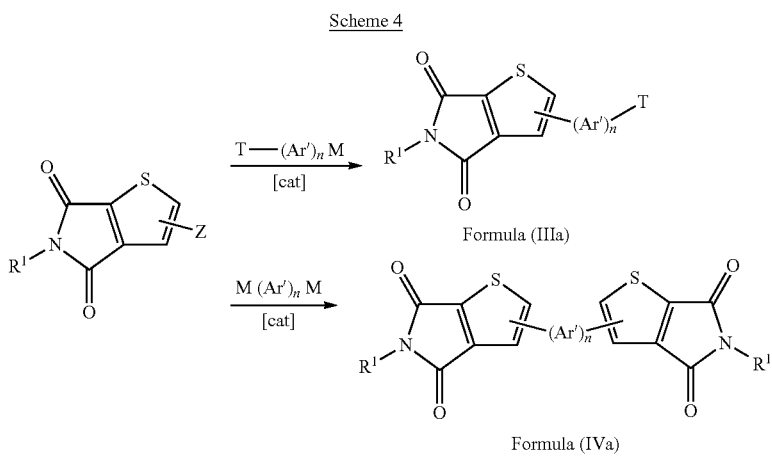

wherein Z is selected among halogen atoms, such as Br, I; M is an organometal compound such as $B(OR')_2$ and $SnR''_3$ wherein R' is selected in the group consisting of hydrogen and alkyl moieties, and R'' is selected in the group consisting of alkyl moieties; and [cat] is a palladium based catalyst. For example, tetrakis triphenylphosphine palladium (0) can be used as catalyst.

According to an alternative synthetic process, direct arylation reaction could be used in place of conventional cross-coupling. In this case, no organometallic species (Ar-M) are required since this reaction typically involves a halogenated framework (Ar—Z) and an unsubstituted one (Ar'—H).

Scheme 3a shows a synthetic approach for the preparation of the starting material of Scheme 3, wherein NZS is a halogenated succinimide.

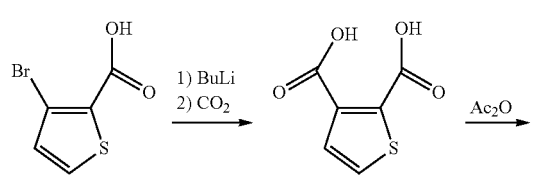

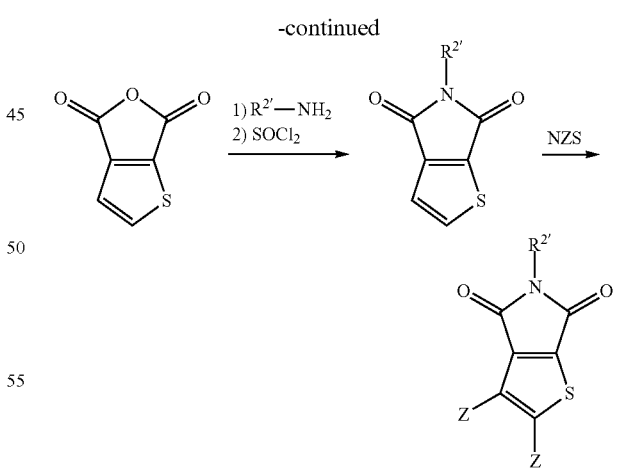

The molecular symmetry of the compounds affects the self-organization motifs and morphology of the molecules in the solid state, thus the final functional properties. In the above schemes, the symmetry of the final compounds can be controlled by changing the synthetic approach. Cross-coupling reaction between mono-halogenated thiophene-imide unit and monometallic species or direct arylation between monohalogen and unsubstituted thieno(imide), lead to asymmetric systems (Ia) and (IIIa). On the other hand, by using bimetallic or bihalogenated species a symmetric system can be obtained, provided that the N-substituting groups $R^1$ and $R^2$ are the same.

In detail, the synthesis of a preferred compound 5, of formula (VI) according to the present invention, is outlined in the following Scheme 5.

pling of compound 4 with bistannyl-bithiophene leads to desired compound 5 in satisfying yield.

In another aspect thereof, the present invention relates to a semiconductor material, comprising at least one compound according to formulas (I); (II); (III); and/or (IV). Preferably, said semiconductor material comprises at least one compound according to formulas (Ia); (IIa); (IIIa); and/or (IVa).

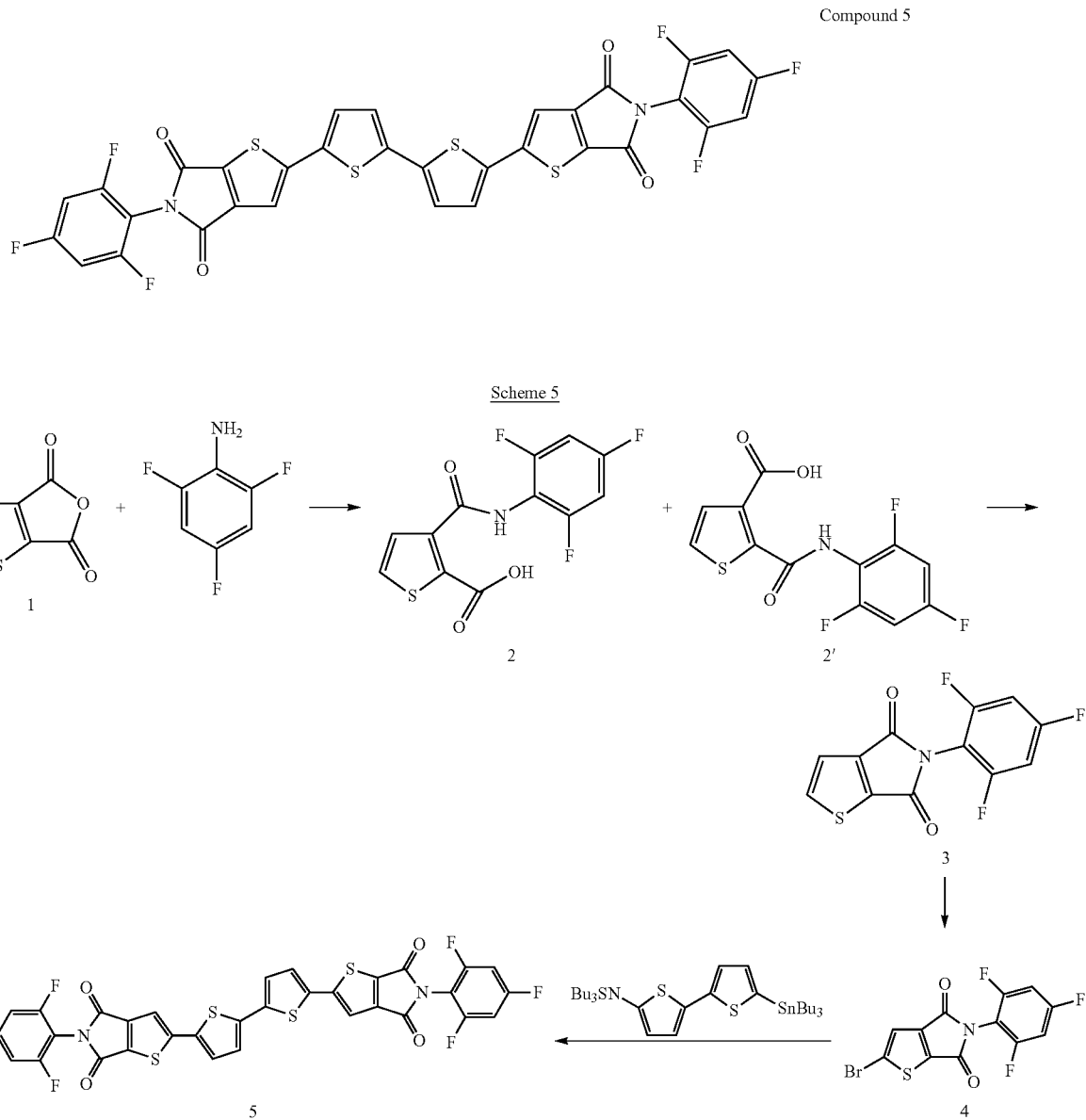

Scheme 5 outlines the preparation of compound 5 according to the present invention, a thiophene based oligomer in which the aromatic core Ar' consists of a 2,2'-bithiophene, the terminals are symmetric imide moieties bearing 2,4,6-trifluorophenyl groups as N-substituents. The synthetic route to the target oligomer is based on the Stille cross coupling reaction between a bistannyl-bithiophene and the brominated thiophene-imide block 4 under conventional heating. In detail, the thiophene-imide starting unit 3 can be prepared by the corresponding anhydride 1, following prior art processes. Bromination of 3 and subsequent Stille cross-cou- More preferably, said semiconductor material, comprises at least one compound according to formulas (V), (VI), (VII) and/or (VIIa).

In an embodiment thereof, said semiconductor material comprises compound 5.

According to another aspect, the invention relates to an electronic device comprising a semiconductor layer in contact with a number of electrodes, wherein the semiconductor layer includes at least one compound according to formulas (I); (II); (III); and/or (IV). Preferably, said semiconductor layer comprises at least one compound according to formulas (Ia); (IIa); (IIIa); and/or (IVa). More preferably, said semiconductor layer, comprises at least one compound according to formulas (V), (VI) and/or (VII).

In an embodiment thereof, said semiconductor layer comprises compound 5.

Preferably, said electronic device comprising a semiconductor layer including the compounds according to the present invention is selected among optical devices, electrooptical devices, field effect transistors, integrated circuit, thin film transistors, organic light-emitting devices, and organic solar cells.

Particularly, thin films of the thiophene-imide based materials according to the invention can be used as active layers in OFETs and OLET devices as demonstrated in the following examples. They can be used as electron- or hole-transporting layer or ambipolar transporters in single layer OFET, as multifunctional electron- and hole-transporting and light emitting layer in single layer OLET, and as hole or electron transporting layer in multi-layer OLET.

Finally, applications of compounds and materials according to the present invention in organic photovoltaics can be envisaged.

In the following examples, all $^1$H, $^{13}$C, and $^{19}$F NMR spectra were recorded at room temperature on a Varian Mercury 400 spectrometer operating at 400 MHz ($^1$H) and 100.6 MHz ($^{13}$C). Chemical shifts were calibrated using the internal CDCl$_3$, acetone-d$_6$ or CD$_2$Cl$_2$ resonance which were referenced to TMS. In the $^{19}$F NMR spectra 0.5% fluorobenzene was added as an internal standard. The fluorobenzene was referenced to CFCl$_3$. Mass spectra were collected on quadrupole ISQ Thermoscientific spectrometer. Each sample was introduced to the ion source region of the ISQ via a direct exposure probe (DEP). Melting points (uncorrected) were determined on a 'hot-stage' apparatus where the melting process was observed with the aid of a microscope. UV-Vis spectra were recorded using a Perkin Elmer Lambda 20 spectrometer. Photoluminescence spectra were obtained with a Perkin Elmer LS50B spectrofluorometer using an excitation wavelength corresponding to the maximum absorption lambda.

2,4,6-Trifluoroaniline and 5,5'-bis(tributylstannyl)-2,2'-bithiophene were purchased from Sigma-Aldrich Co. Thiophene-2,3-dicarboxylic anhydride, 1 was prepared according to already reported procedures.

Example 1

Synthesis of 3-(2,4,6-trifluorophenylcarbamoyl) thiophene-2-carboxylic acid, 2 and 2-(2,4,6-trifluorophenyl carbamoyl)thiophene-3-carboxylic acid, 2'

A solution of thiophene-2,3-dicarboxylic anhydride, 1 (308 mg, 2 mmol) and 2,4,6-trifluoroaniline (309 mg, 2.1 mmol) in 20 ml of toluene was refluxed for 24 h. The crude products were collected by filtration of the cold reaction mixture. Crystallization from toluene afforded a mixture of the title isomers in a 2:1 ratio (500 mg, 83% yield) as a white solid which was used in the next cyclization step without further purification. MS (70 eV, EI): m/z 301 (M.$^{+1}$), $^1$H NMR (aceton-d$_6$, TMS/ppm) δ major isomer 7.96 (d, $^3$J=5.6 Hz, 1H), 7.89 (d, $^3$J=5.6 Hz, 1H), 7.13 (m, 2H); δ minor isomer 7.87 (d, $^3$J=5.6 Hz, 1H), 7.75 (d, $^3$J=5.6 Hz, 1H), 7.09 (m, 2H).

Example 2

Synthesis of 5-(2,4,6-trifluorophenyl)-5H-thieno[2, 3-c]pyrrole-4,6-dione 3

A solution of 2+2' (482 mg, 1.6 mmol) in 32 ml of thionyl chloride was refluxed for 3 h. The solvent was removed by distillation and the resulting brown solid purified by flash chromatography (silica gel, pet. eth./CH$_2$Cl$_2$/AcOEt 8:1:1) to afford the title compound as a beige crystalline solid (406 mg, 90%). M.p. 199° C.; MS (70 eV, EI): m/z 283 (M.$^{+1}$), $^1$H NMR (CDCl$_3$, TMS/ppm) δ 7.88 (d, $^3$J=4.8 Hz, 1H), 7.43 (d, $^3$J=4.8 Hz, 1H), 6.85 (m, 2H); $^{13}$C NMR (CDCl$_3$, TMS/ppm) δ 161.7, 160.0, 144.7, 140.9, 138.6, 121.8, 101.3, 101.1; δ $^{19}$F NMR (CDCl$_3$, CFCl$_3$/ppm) δ-104.6 (m, 1F), −113.5 (m, 2F).

Example 3

Synthesis of 2-bromo-5-(2,4,6-trifluorophenyl)-5H-thieno[2,3-c]pyrrole-4,6-dione, 4

Compound 3 (400 mg, 1.41 mmol) was dissolved in 6 ml of trifluoroacetic acid. After external ice cooling, 1 ml of concentrated sulfuric acid was introduced into the reactor. To this mixture was added solid NBS (244 mg, 1.37 mmol) in small portions over 6 hs. After stirring overnight at room temperature, the brown solution was diluted with 10 ml of water and extracted with dichloromethane. The organic phase was dried over anhydrous magnesium sulfate and evaporated to afford the crude product as a brown solid. Purification by column chromatography using silica gel and pet. eth./AcOEt (90:10) as eluent gave 350 mg (69%) of the desired compound as off-white crystals. M.p. 192° C.; MS (70 eV, EI): m/z 361 (M.$^{+1}$); $^1$H NMR (CDCl$_3$, TMS/ppm) δ 7.44 (s, 1H), 6.85 (m, 2H); $^{13}$C NMR (CDCl$_3$, TMS/ppm) δ 161.8, 160.1, 144.0, 140.5, 127.2, 124.4, 101.4, 101.1; $^{19}$F NMR (CDCl$_3$, CFCl$_3$/ppm) δ-104.2 (m, 1F), −113.4 (m, 2F).

Example 4

Synthesis of 2,2'-(2,2'-bithiophene-5,5'-diyl)bis(5-(2, 4,6-trifluorophenyl)-5H-thieno[2,3-c]pyrrole-4,6-dione), 5

To a refluxing xilene solution (8 ml) of compound 4 (152 mg, 0.42 mmol) and in-situ prepared catalyst Pd(AsPh$_3$)$_4$ (10 mol %, i.e. 21.7 mg of Pd$_2$ dba$_3$ and 51.4 mg of AsPh$_3$) under N$_2$ atmosphere, 5,5'-bis(tributylstannyl)-2,2'-bithiophene (153 mg, 0.20 mmol) in xilene (2 ml), was added drop wise. The solution was refluxed for 6 h then the solvent was removed under vacuum, and the crude product was washed with pentane and isopropanol. Crystallization from hot toluene gave the product as a dark red solid (74 mg, 51%). M.p. 334° C., MS (70 eV, EI): m/z 728 (M.$^{-1}$), absorption maximum, 457 nm, emission maximum, 578 nm in DCM; $^1$H NMR (CD$_2$Cl$_2$, TMS/ppm) δ 7.49 (s, 2H), 7.40 (d, $^3$J=4.0 Hz, 2H), 7.30 (d, $^3$J=4.0 Hz, 2H), 6.92 (m, 4H); $^{19}$F NMR (CDCl$_3$, CFCl$_3$/ppm) δ−105.3 (m, 2F), −114.0 (m, 4F), −105.3 (m, 2F), −114.0 (m, 4F). Anal. Calcd for C$_{32}$H$_{10}$F$_6$N$_2$O$_4$S$_4$ (728.68): C, 52.74; H, 1.38. Found: C, 52.79; H, 1.34.

Example 5

Fabrication of an Organic Thin Film Transistor

An organic thin film transistor (OTFT) was fabricated in bottom gate-top contact geometry. The ITO substrate cleaning procedure used consist of two sonication cycles, in acetone first and 2-isopropanol then, for 10 minutes each. The 450 nm thick dielectric layer of PMMA has been grown by spin-coating on top of the clean ITO substrate (relative electric permittivity ∈=3.6 at 100 Hz). The PMMA film was then thermally annealed in a glove box at 120° C. (around 10° C. above the glass transition temperature for PMMA) for 15 hours under inert atmosphere. The 15 nm thick layer of compound 5 was grown by vacuum sublimation in a homemade vacuum chamber, with a deposition rate of 0.1 Å/s, at a base pressure of $10^{-6}$ mbar. Gold source-drain contacts are then deposited on top of the organic film, properly masked to form a 70 μm length and a 15 mm width channel. The substrate temperature during the film deposition has been kept at room temperature (RT).

The electrical measurements are performed by means of a Suss PM5 professional probe station connected with an Agilent B1500A parametric analyzer located inside a dry inert glove box. The probe station has been equipped with a Hamamatsu S1337 photodiode with an active area of 1 cm², located under the OTFT channel, in order to collect the electroluminescence originating from the working device. Further device features were:

$C_{PMMA}$=7.08 nF/cm²

Figure 4:
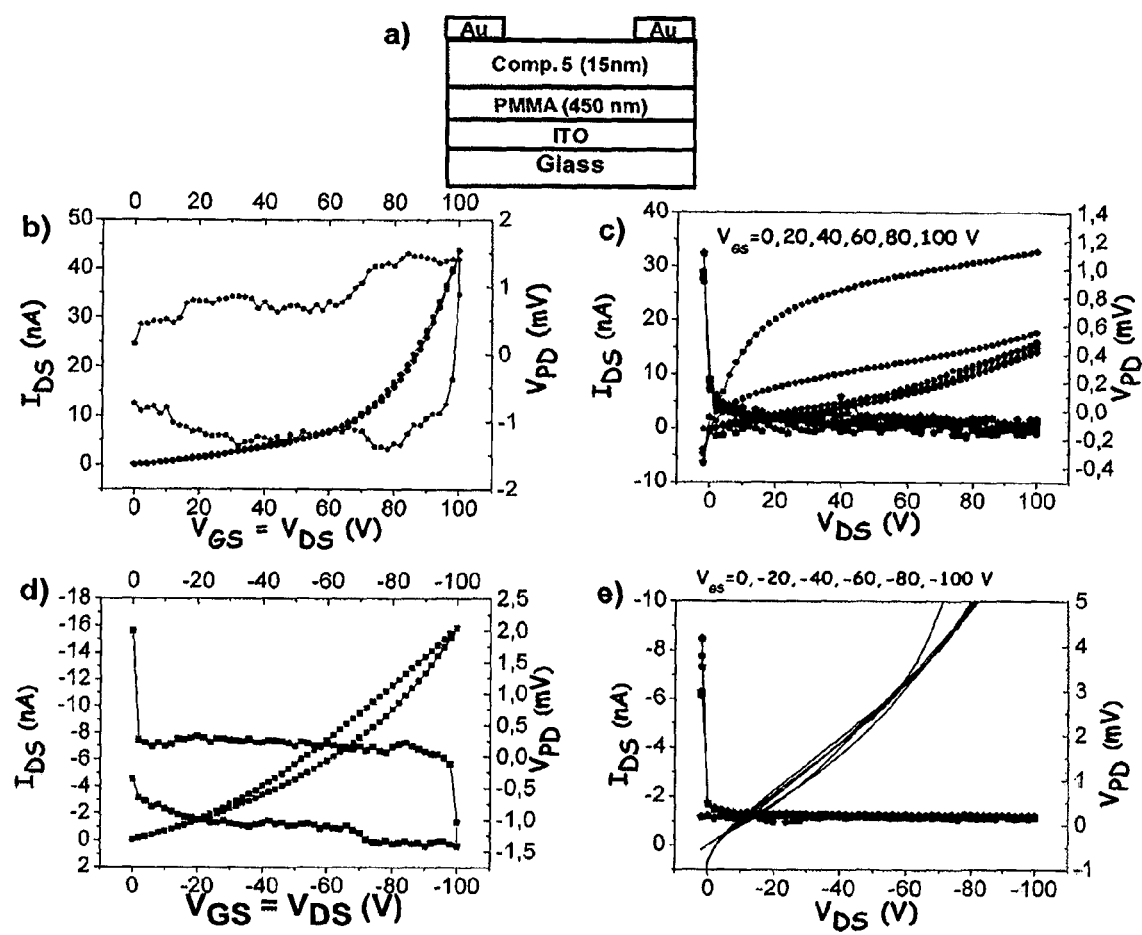
FIG. 4 a), b), c), d), and e) show graphs reporting the optoelectronic features of an OTFT comprising compound 5 according to the present invention as semiconductor layer.

The electrical response of the fabricated OTFT has been measured in nitrogen controlled atmosphere, using a commercial probe station Suss PM5 professional probe station equipped with a photodiode in order to collect possible electroluminescence originating from the working device. The probe station is integrated with a B1500 Agilent parametric analyzer. The obtained results consist in the graphs reported in FIG. 4, wherein charge mobility and threshold voltage measured values measured are the following:

$\mu_N$=2.5 $10^{-5}$ cm²/Vs
$V_T^N$=50V
$\mu_P$=1.3 $10^{-6}$ cm²/Vs
$V_T^P$=−10V

Example 6

Synthesis of 2-(2,2'-bithiophen-5-yl)-5-(3-chloro-2,4,6-trimethylphenyl)-5H-thieno[2,3-c]pyrrole-4,6-dione, compound 8 a) Preparation of 2-(mesitylcarbamoyl)thiophene-3-carboxylic acid and 3-(mesitylcarbamoyl)thiophene-2-carboxylic acid, 6-6'

To a solution of 1 (1.1 g, 0.0071 mol) in 110 ml of dry toluene, 2,4,6-trimethylphenylamine (1.013 g, 0.0075 mol) was added at room temperature and the mixture was refluxed for 48 h. After cooling to room temperature, the solid formed was collected and washed with pentane. A whity solid was obtained (2 g, yield 97%).

MS (70 eV, EI) m/z 289 (M.⁺). ¹H NMR (CDCl₃, TMS/ppm) δ 9.49 (bs, 1H), 8.49 (bs, 1H), 7.76 (d, ³J=5.6 Hz, 1H), 7.67 (d, ³J=5.6 Hz, 1H), 7.61 (d, ³J=5.6 Hz, 1H), 7.46 (d, ³J=5.6 Hz, 1H), 6.94 (s, 2H), 6.92 (s, 2H), 2.30 (s, 3H), 2.28 (s, 3H), 2.22 (s, 6H), 2.21 (s, 6H).

b) Preparation of 5-(3-chloro-2,4,6-trimethylphenyl)-5H-thieno[2,3-c]pyrrole-4,6-dione, 7

A solution of 6-6' mix (2.0 g; 0.0069 mol) in SOCl₂ (100 ml) was refluxed under N₂ for 5 h. After removing of SOCl₂ by distillation, the crude product was purified by flash chromatography on silica gel (elution with petroleum ether 40/70:CH₂Cl₂:AcOEt/40:30:30). Compound 7 was obtained as a whity solid (0.58 g, yield 27%).

MS (70 eV, EI) m/z 305, 307 (M.⁺), ¹H NMR (CDCl₃, TMS/ppm) δ 7.87 (d, ³J=4.8 Hz, 1H), 7.42 (d, ³J=4.8 Hz, 1H), 7.09 (s, 1H), 2.39 (s, 3H), 2.23 (s, 3H), 2.13 (s, 3H).

c) Preparation of 2-(2,2'-bithiophen-5-yl)-5-(3-chloro-2,4,6-trimethylphenyl)-5H-thieno[2,3-c]pyrrole-4,6-dione, 8

A mixture of 7 (0.250 g, 0.000817 mol), 5-bromo-2,2'-bithiophene (0.260 g, 0.00106 mol), pivalic acid (0.025 g, 0.000245 mol), K₂CO₃ (0.169 g, 0.00123 mol), Pd(OAc)₂ (0.011 g, 0.000049 mol), PCy₃HBF₄ (0.036 g, 0.000098 mol) in 2.5 ml of dry toluene was refluxed for 5 h. After solvent evaporation, the mixture was dissolved in 15 ml of CH₂Cl₂ and washed with water. The organic layer was Scheme 6

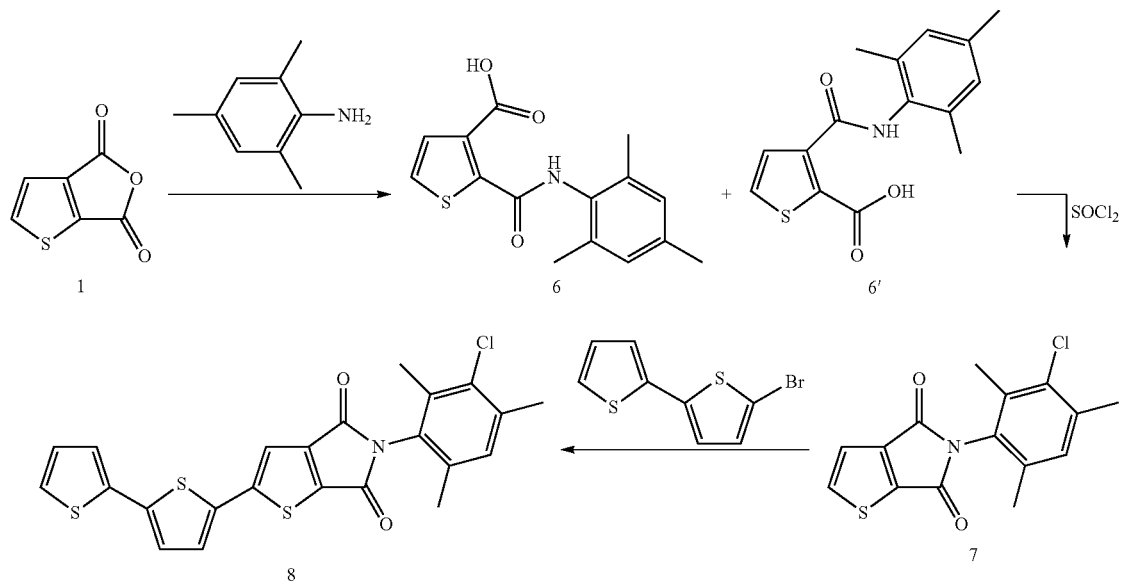

evaporated and the crude product was purified by flash chromatography on silica gel (elution with petroleum ether 40/70:CH$_2$Cl$_2$:AcOEt/80:10:10). The fractions containing the product were combined, the solvent evaporated, and the residue crystallized from hot toluene. Compound 8 was obtained as a dark orange solid (80 mg, yield 21%).

M.p. 185° C. EI-MS m/z 469, 471 (M.$^+$). $\lambda_{max}$ (CH$_2$Cl$_2$), 425 nm, $\lambda_{em}$ (CH$_2$Cl$_2$), 576 nm.

$^1$H NMR (CDCl$_3$, TMS/ppm) δ 7.41 (s, 1H), 7.30 (d, $^3$J=4.0 Hz, 1H), 7.29 (d, $^3$J=4.0 Hz, 1H), 7.25 (d, $^3$J=3.2 Hz, 1H), 7.16 (d, $^3$J=3.6 Hz, 1H), 7.09 (s, 1H), 7.06 (dd, $^3$J=4.8 Hz $^3$J=5.2 Hz, 1H) 2.39 (s, 3H), 2.24 (s, 3H), 2.14 (s, 3H). $^{13}$C NMR (CDCl$_3$, TMS/ppm) δ 162.6, 161.5, 150.9, 145.1, 139.8, 137.9, 136.8, 136.1, 135.7, 135.3, 133.3, 132.9, 130.1, 128.5, 128.1, 127.1, 125.7, 124.8, 124.7, 116.7, 20.9, 17.9, 16.2.

Example 7

Synthesis of 2,2'-(5,5'-(5-butyl-4,6-dioxo-5,6-dihydro-4H-thieno[3,4-c]pyrrole-1,3-diyl)bis(thiophene-5,2-diyl))bis(5-(3-chloro-2,4,6-trimethylphenyl)-5H-thieno[2,3-c]pyrrole-4,6-dione,)

a) Preparation of 5-(3-chloro-2,4,6-trimethylphenyl)-2-(thiophen-2-yl)-5H-thieno[2,3-c]pyrrole-4,6-dione, 9

A mixture of 7 (0.325 g, 0.000106 mol), 2-bromothiophene (0.225 g, 0.00138 mol), pivalic acid (0.065 g, 0.000637 mol), K$_2$CO$_3$ (0.147 g, 0.00106 mol), Pd(OAc)$_2$ (0.014 g, 0.0000637 mol), PCy$_3$HBF$_4$ (0.047 g, 0.000127 mol) in 6 ml of dry toluene was refluxed for 5 h. After solvent evaporation, the mixture was dissolved in 20 ml of CH$_2$Cl$_2$ and washed with water. The organic layer was evaporated and the crude product was purified by flash chromatography on silica gel with (petroleum ether 40/70: CH$_2$Cl$_2$:EtOAc/80:10:10). Product 9 was obtained as an orange solid (230 mg, yield 56%). MS (70 eV, EI) m/z 387, 389 (M.$^+$), $^1$H NMR (CDCl$_3$, TMS/ppm) δ 7.43 (s, 1H), 7.42 (dd, $^3$J=5.2 Hz, $^4$J=1.2 Hz, 1H), 7.38 (dd, $^3$J=4.0 Hz, $^4$J=0.8 Hz, 1H), 7.12 (q, $^3$J=5.2 Hz, $^3$J=4.8 Hz, 1H), 7.09 (s, 1H), 2.39 (s, 3H), 2.24 (s, 3H), 2.14 (s, 3H).

b) Preparation of 2-(5-bromothiophen-2-yl)-5-(3-chloro-2,4,6-trimethylphenyl)-5H-thieno[2,3-c]pyrrole-4,6-dione, 10

Compound 9 (0.235 g, 0.606 mmol) was dissolved in 30 ml of a 1:1 mixture of dichloromethane and acetic acid and,

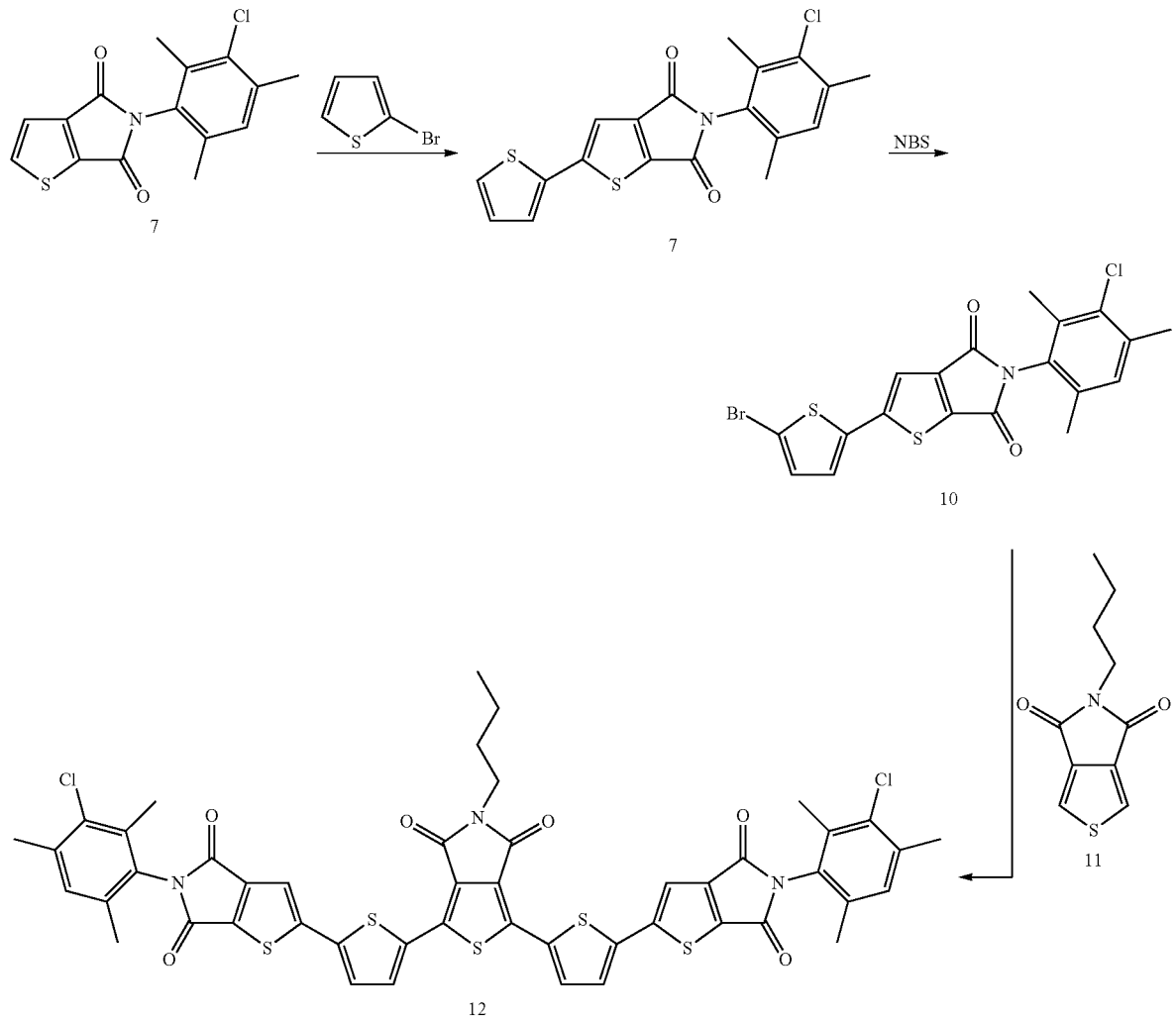

Scheme 7 after 10 minutes 0.5 ml H$_2$SO$_4$ 98% was added. At 0° C., under exclusion of light, NBS (119 mg, 0.666 mmol) was added and the reaction mixture was stirred at room temperature overnight. The yellow solution was then diluted with 50 ml of water and extracted with dichloromethane. The organic layer was evaporated and dried over Na$_2$SO$_4$. The crude product was purified by flash chromatography on silica gel (elution with petroleum ether 40/70:CH$_2$Cl$_2$: AcOEt/80:10:10) to afford compound 10 as a yellow powder (229 mg, yield 81%).

MS (70 eV, EI) m/z 467 (M.$^+$). $^1$H NMR (CDCl$_3$, TMS/ppm) δ 7.36 (s, 1H), 7.13 (d, $^3$J=3.6 Hz, 1H), 7.08 (s, 1H), 7.07 (d, $^3$J=4.0 Hz, 1H), 2.39 (s, 3H), 2.23 (s, 3H), 2.13 (s, 3H).

c) Preparation of 2,2'-(5,5'-(5-butyl-4,6-dioxo-5,6-dihydro-4H-thieno[3,4-c]pyrrole-1,3-diyl)bis(thiophene-5,2-diyl))bis(5-(3-chloro-2,4,6-trimethylphenyl)-5H-thieno[2,3-c]pyrrole-4,6-dione,) 12

A mixture of 10 (0.229 g, 0.490 mmol), 11 (0.049 g, 0.234 mmol), pivalic acid (0.029 g, 0.28 mmol), K$_2$CO$_3$ (0.097 g, 0.701 mmol), Pd(OAc)$_2$ (3 mg, 0.0140 mmol), PCy$_3$HBF$_4$ (10 mg, 0.028 mmol) in 10 ml of dry toluene was refluxed for 5 h. After solvent evaporation, the mixture was dissolved in 15 ml of CH$_2$Cl$_2$ and washed with water. The organic layer was evaporated and the crude product was purified by flash chromatography on silica gel (petroleum ether 40/70: CH$_2$Cl$_2$:EtOAc/60:30:10). The fractions containing the product were combined, the solvent evaporated, and the residue crystallized from hot dichloromethane and washed at −50° C. with pentane. Compound 12 was obtained as a red solid (70 mg, yield 30%).

M.p. 235° C. MS (70 eV, EI) m/z 981 (M.$^+$). λ$_{abs, max}$ (CH$_2$Cl$_2$), 460 nm, λ$_{em}$ (CH$_2$Cl$_2$), 545 nm. $^1$H NMR (CDCl$_3$, TMS/ppm) δ 8.02 (d, $^3$J=4.0 Hz, 2H), 7.53 (s, 2H), 7.40 (d, $^3$J=4.0 Hz, 2H), 7.10 (s, 2H), 3.72 (t, 2H), 2.40 (s, 6H), 2.24 (s, 6H), 2.15 (s, 6H), 1.70 (m, 2H), 1.42 (m, 2H), 0.98 (t, 3H). $^{13}$C NMR (CDCl$_3$, TMS/ppm) δ 162.3, 162.3, 161.2, 149.5, 145.0, 138.2, 138.0, 137.8, 135.6, 135.3, 135.2, 133.8, 132.9, 131.1, 130.1, 129.9, 128.4, 127.3, 117.9, 38.6, 30.5, 20.9, 20.2, 17.9, 16.2, 13.7.

The invention claimed is:

1. A compound having formula selected from the group consisting of formula (III) and formula (IV):

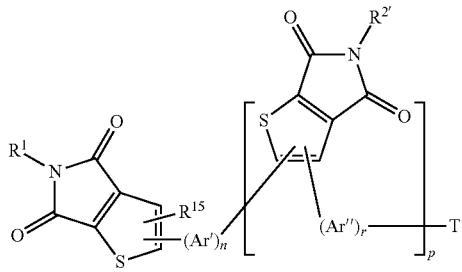

formula (III)

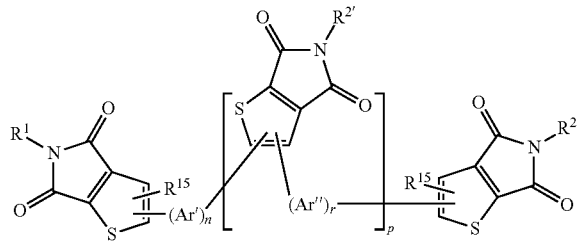

formula (IV)

wherein:
R$^{2'}$, R$^1$, and R$^2$, independently of each other, are selected from the group consisting of phenyl group, substituted phenyl groups, benzyl groups and substituted benzyl groups;
Ar', and Ar'', independently of each other, are moieties selected from the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers;
R$^{15}$ is selected from the group consisting of hydrogen, halogen, C$_1$-C$_{20}$ linear or branched alkyl groups, C$_1$-C$_{20}$ linear or branched heteroalkyl groups, C$_1$-C$_{20}$ linear or branched heteroalkoxyalkyl groups, C$_1$-C$_{20}$ linear or branched halogenoalkyl groups, C$_3$-C$_{20}$ linear or branched cycloalkyl groups, C$_1$-C$_{20}$ linear or branched hydroxyalkyl groups, C$_1$-C$_{20}$ linear or branched alkoxyl groups and C$_1$-C$_{20}$ linear or branched nitrile groups;
n, r, independently of each other, are integers between 1 and 50;
p is an integer between 0 and 5; and
T is a terminal unit of the compound and is selected among hydrogen, C$_1$-C$_{40}$ linear or branched alkyl groups, C$_1$-C$_{40}$ linear or branched haloalkyl groups, C$_1$-C$_{40}$ linear or branched heteroalkyl groups, C$_3$-C$_{40}$ linear or branched cycloalkyl groups, C$_1$-C$_{40}$ linear or branched hydroxyalkyl groups, C$_1$-C$_{40}$ linear or branched alkoxyl groups, C$_1$-C$_{40}$ linear or branched heteroalkoxyalkyl groups, C$_1$-C$_{40}$ linear or branched alkylcarboxylic groups, C$_1$-C$_{40}$ linear or branched alkylcarboxyamide groups, C$_1$-C$_{40}$ linear or branched alkylsulphonic groups, and C$_1$-C$_{40}$ linear or branched nitrile groups, monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers;
with the exception of compounds of formula A:

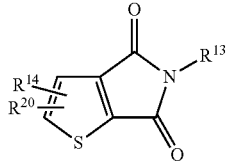

formula A wherein $R^{13}$ is selected from the group consisting of phenyl, 4-chlorophenyl, 3-trifluoromethylphenyl; $R^{14}$ is selected from the group consisting of phenyl, 2-fluorphenyl, 3-fluorphenyl, 4-fluorphenyl, 2-chlorphenyl, 3-chlorphenyl, 4-chlorphenyl, 2-methylphenyl, 3-methylphenyl, 4-methylphenyl, 2-trifluoromethylphenyl, 3-trifluormethylphenyl, 4-trifluormethylphenyl, 2-methoxyphenyl, 3-methoxyphenyl, 4-methoxyphenyl, 2,4-dichlorphenyl, 2,4,6-trimethylphenyl, 2-thienyl, 3-thienyl, 2-pyridyl, 3-pyridyl, 4-pyridyl; and $R^{20}$ is selected from the group consisting of H, Cl, F, methyl, and methoxy.

2. The compound according to claim 1, wherein when p is 0, n is between 2 and 50.

3. The compound according to claim 1, having formula selected from the group consisting of formula (IIIa) and formula (IVa)

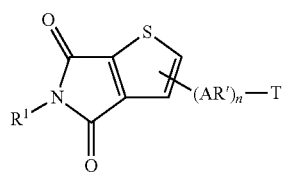

formula (IIIa)

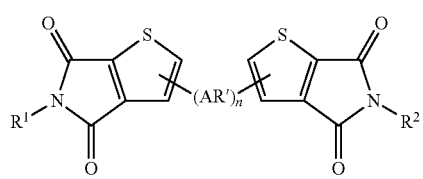

formula (IVa)

wherein:
- $R^1$, and $R^2$, independently of each other, are selected from the group consisting of phenyl group, substituted phenyl groups, benzyl groups and substituted benzyl groups;
- Ar', is a moiety selected from the group consisting of a monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers; and
- T is a terminal unit of the compound and is selected among hydrogen, $C_1$-$C_{40}$ linear or branched alkyl groups, $C_1$-$C_{40}$ linear or branched haloalkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups, monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers.

4. The compound according to claim 1, wherein Ar' is a unit selected from the group consisting of the following units (a), (b), (c), (d), (e), (f), (g), (h), (i), (l), (m), (n), (o), (p), (q), and (r):

(a)

(b)

(c)

(d)

(e)

(f)

(g)

-continued

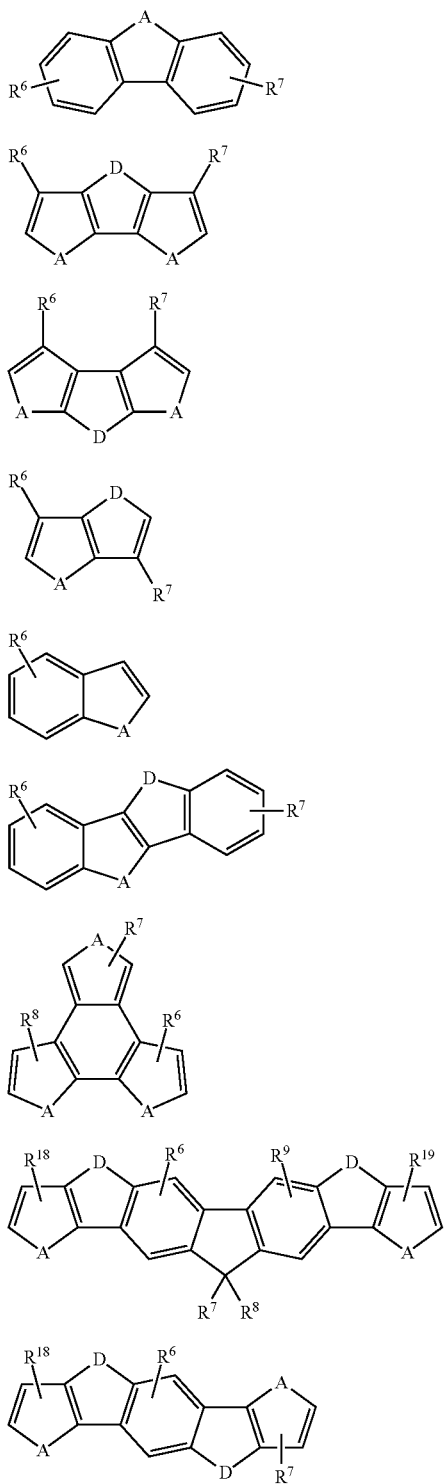

wherein A is selected from the group consisting of S, O, Se, atoms and SO, SO$_2$, R$^{17}$—P=O, P—(R$^{17}$)$_2$, N—R$^{16}$, and Si(R$^{16}$)$_2$ groups;

D is selected from the group consisting of S, O, Se, atoms and SO, SO$_2$, R$^{17}$—P=O, P—(R$^{17}$)$_2$, N—R$^{16}$, and Si(R$^{16}$)$_2$ groups;

B and C, independently of each other, are NR$^{16}$ group;

E is selected from the group consisting of C(R$^{16}$)$_2$, S, O, and NR$^{16}$ group;

R$^6$, R$^7$, R$^8$, R$^9$, R$^{18}$ and R$^{19}$, independently of each other, are selected from the group consisting of hydrogen, halogens, C$_1$-C$_{20}$ linear or branched alkyl groups, C$_2$-C$_{20}$ linear or branched alkenyl groups, C$_3$-C$_{20}$ linear or branched alkyl-alkenyl groups, C$_1$-C$_{20}$ linear or branched halogenoalkyl groups, C$_2$-C$_{20}$ linear or branched alkynyl groups, C$_3$-C$_{20}$ linear or branched alkyl-alkynyl groups, C$_3$-C$_{20}$ linear or branched cycloalkyl groups, C$_1$-C$_{20}$ linear or branched hydroxyalkyl groups, C$_1$-C$_{20}$ linear or branched alkoxyl groups, C$_1$-C$_{20}$ linear or branched heteroalkoxyalkyl groups, C$_1$-C$_{20}$ linear or branched alkylcarboxylic groups, C$_1$-C$_{20}$ linear or branched alkylcarboxyamide groups, C$_1$-C$_{20}$ linear or branched alkylsulphonic groups, C$_1$-C$_{20}$ linear or branched nitrile groups, C$_5$-C$_{40}$ aryl groups, and C$_6$-C$_{40}$ alkylaryl groups;

R$^{16}$ and R$^{17}$ independently of each other, are selected from the group consisting of hydrogen, C$_1$-C$_{20}$ linear or branched alkyl groups, C$_2$-C$_{20}$ linear or branched alkenyl groups, C$_3$-C$_{20}$ linear or branched alkyl-alkenyl groups, C$_1$-C$_{20}$ linear or branched halogenoalkyl groups, C$_2$-C$_{20}$ linear or branched alkynyl groups, C$_3$-C$_{20}$ linear or branched alkyl-alkynyl groups, C$_3$-C$_{20}$ linear or branched cycloalkyl groups, C$_1$-C$_{20}$ linear or branched hydroxyalkyl groups, C$_1$-C$_{20}$ linear or branched alkoxyl groups, C$_1$-C$_{20}$ linear or branched heteroalkoxyalkyl groups, C$_1$-C$_{20}$ linear or branched alkylcarboxylic groups, C$_1$-C$_{20}$ linear or branched alkylcarboxyamide groups, C$_1$-C$_{20}$ linear or branched alkylsulphonic groups, C$_1$-C$_{20}$ linear or branched nitrile groups, C$_5$-C$_{40}$ aryl groups, and C$_6$-C$_{40}$ alkylaryl groups.

5. The compound according to claim 1, wherein the [Ar']$_n$ unit is selected from the group consisting of the following groups (s) and (t):

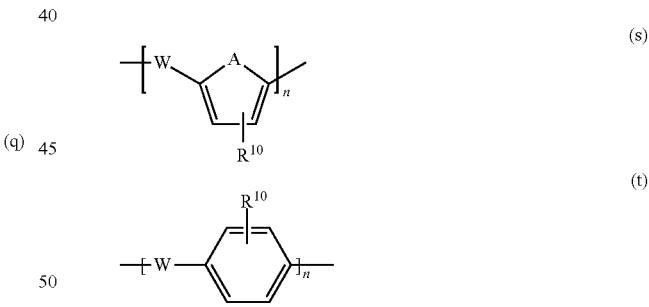

wherein A is selected from the group consisting of S, O, Se, atoms and SO, SO$_2$, R$^{17}$—P=O, P—(R$^{17}$)$_2$, N—R$^{16}$, and Si(R$^{16}$)$_2$ groups;

R$^{16}$, R$^{17}$ independently of each other, are selected in the group consisting of hydrogen, C$_1$-C$_{20}$ linear or branched alkyl groups, C$_2$-C$_{20}$ linear or branched alkenyl groups, C$_3$-C$_{20}$ linear or branched alkyl-alkenyl groups, C$_1$-C$_{20}$ linear or branched halogenoalkyl groups, C$_2$-C$_{20}$ linear or branched alkynyl groups, C$_3$-C$_{20}$ linear or branched alkyl-alkynyl groups, C$_3$-C$_{20}$ linear or branched cycloalkyl groups, C$_1$-C$_{20}$ linear or branched hydroxyalkyl groups, C$_1$-C$_{20}$ linear or branched alkoxyl groups, C$_1$-C$_{20}$ linear or branched heteroalkoxyalkyl groups, C$_1$-C$_{20}$ linear or branched alkylcarboxylic groups, C$_1$-C$_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups;

W is a moiety selected from the group consisting of the units (a), (b), (c), (d), (e), (f), (g), (h), (i), (l), (m), (n), (o), (p), (q), and (r);

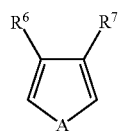
(a)

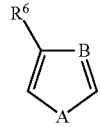
(b)

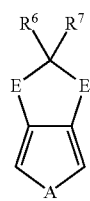
(c)

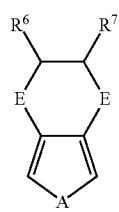
(d)

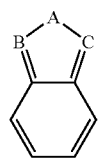
(e)

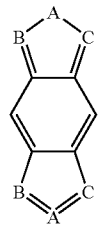
(f)

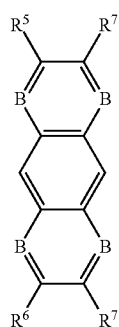
(g)

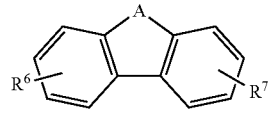
(h)

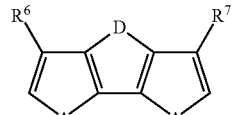
(i)

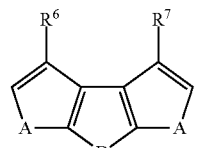
(l)

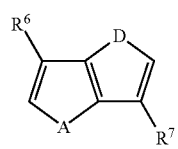
(m)

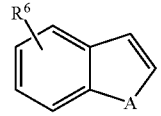
(n)

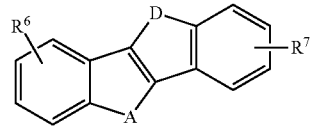
(o)

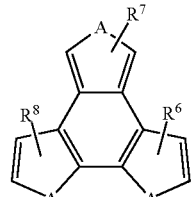
(p)

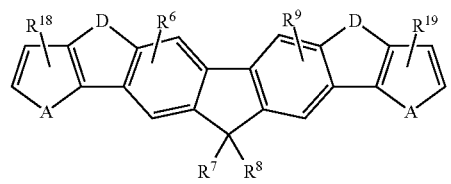
(q)

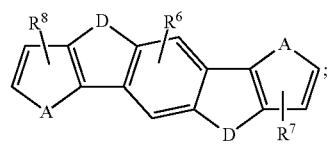
(r)

wherein D is selected from the group consisting of S, O, Se, atoms and SO, $SO_2$, $R^{17}$—P=O, P—$(R^{17})_2$, N—$R^{16}$, and $Si(R^{16})_2$ groups;

B and C, independently of each other, are a $NR^{16}$ group;

E is selected from the group consisting of $C(R^{16})_2$, S, O, and $NR^{16}$ group;

$R^6$, $R^7$, $R^8$, $R^9$, $R^{18}$ and $R^{19}$, independently of each other, are selected from the group consisting of hydrogen, halogens, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups, $R^{16}$ and $R^{17}$ independently of each other, are selected from the group consisting of hydrogen, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups, $R^{10}$ is selected from the group consisting of the group consisting of hydrogen, halogens, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups.

6. The compound according to claim 1 having the following formula (V):

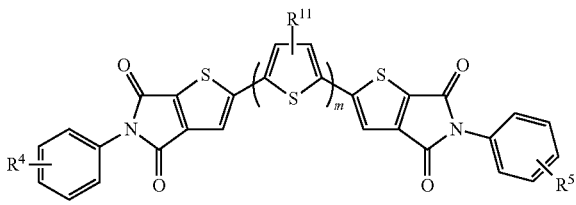

$R^4$, $R^5$, and $R^{11}$, independently of each other, are selected from the group consisting of hydrogen, halogens, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups; and m is an integer between 1 and 50.

7. The compound according to claim 6 having formula (VI):

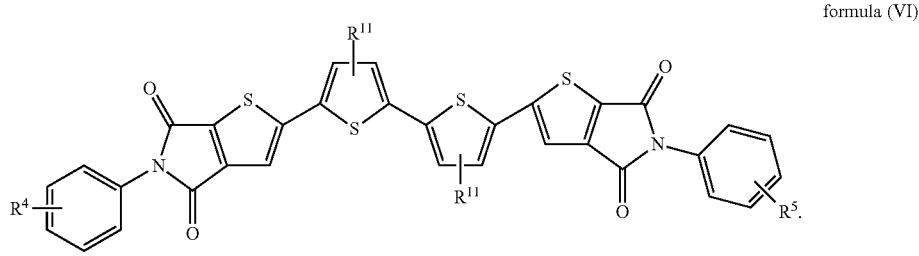

8. The compound according to claim 1 having the following formula (VII):

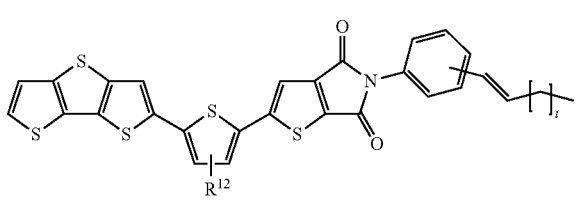

wherein $R^{12}$ is selected from the group consisting of hydrogen, halogens, $C_1$-$C_{20}$ linear or branched alkyl groups, $C_2$-$C_{20}$ linear or branched alkenyl groups, $C_3$-$C_{20}$ linear or branched alkyl-alkenyl groups, $C_1$-$C_{20}$ linear or branched halogenoalkyl groups, $C_2$-$C_{20}$ linear or branched alkynyl groups, $C_3$-$C_{20}$ linear or branched alkyl-alkynyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups, $C_1$-$C_{20}$ linear or branched heteroalkoxyalkyl groups, $C_1$-$C_{20}$ linear or branched alkylcarboxylic groups, $C_1$-$C_{20}$ linear or branched alkylcarboxyamide groups, $C_1$-$C_{20}$ linear or branched alkylsulphonic groups, $C_1$-$C_{20}$ linear or branched nitrile groups, $C_5$-$C_{40}$ aryl groups, and $C_6$-$C_{40}$ alkylaryl groups; and t is an integer between 2 and 6.

9. A method comprising:

providing a compound having formula selected from the group consisting of formula (III) and formula (IV):

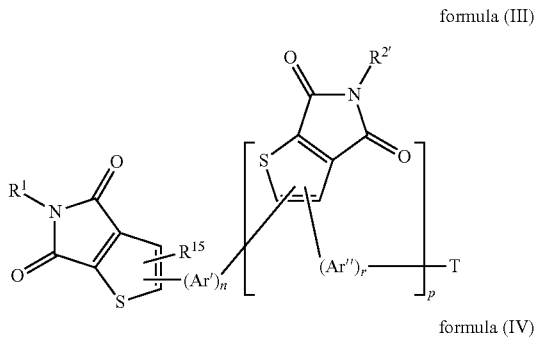

formula (III)

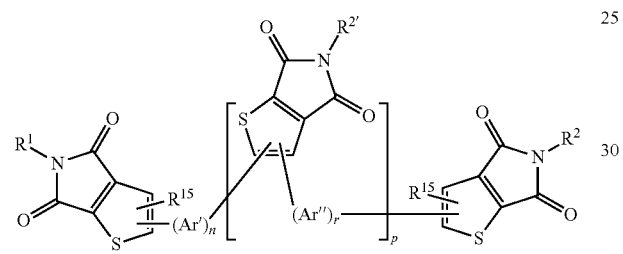

formula (IV)

wherein:

$R^{2'}$, $R^1$, and $R^2$, independently of each other, are selected from the group consisting of phenyl group, substituted phenyl groups, benzyl groups and substituted benzyl groups;

Ar', and Ar", independently of each other, are moieties selected from the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers;

$R^{15}$ is selected from the group consisting of hydrogen, halogen, $C_1$-$C_{20}$ linear or branched alkyl groups, $C_1$-$C_{20}$ linear or branched heteroalkyl groups, $C_1$-$C_{20}$ linear or branched heteroalkoxyalkyl groups, $C_1$-$C_{20}$ linear or branched halogenoalkyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups and $C_1$-$C_{20}$ linear or branched nitrile groups;

n, r, independently of each other, are integers between 1 and 50;

p is an integer between 0 and 5; and

T is a terminal unit of the compound and is selected among hydrogen, $C_1$-$C_{40}$ linear or branched alkyl groups, $C_1$-$C_{40}$ linear or branched haloalkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups, monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers; and using the compound as an organic semiconductor material in an electronic device.

10. The method of claim 9, wherein the organic semiconductor material is an n-type organic semiconductor material.

11. A method comprising:

providing a compound according to claim 2; and using said compound as an organic semiconductor material in an electronic device.

12. An electronic device comprising a semiconductor layer in contact with a number of electrodes, wherein the semiconductor layer includes at least one compound having formula selected from the group consisting of formula (III) and formula (IV):

formula (III)

formula (IV)

wherein:

$R^{2'}$, $R^1$, and $R^2$ independently of each other, are selected from the group consisting of phenyl group, substituted phenyl groups, benzyl groups and substituted benzyl groups;

Ar', and Ar", independently of each other, are moieties selected from the group consisting of monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups and combinations thereof as dimers, trimers and tetramers;

$R^{15}$ is selected from the group consisting of hydrogen, halogen, $C_1$-$C_{20}$ linear or branched alkyl groups, $C_1$-$C_{20}$ linear or branched heteroalkyl groups, $C_1$-$C_{20}$ linear or branched heteroalkoxyalkyl groups, $C_1$-$C_{20}$ linear or branched halogenoalkyl groups, $C_3$-$C_{20}$ linear or branched cycloalkyl groups, $C_1$-$C_{20}$ linear or branched hydroxyalkyl groups, $C_1$-$C_{20}$ linear or branched alkoxyl groups and $C_1$-$C_{20}$ linear or branched nitrile groups;

n, r, independently of each other, are integers between 1 and 50;

p is an integer between 0 and 5; and

T is a terminal unit of the compound and is selected among hydrogen, $C_1$-$C_{40}$ linear or branched alkyl groups, $C_1$-$C_{40}$ linear or branched haloalkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups, monocyclic aryl groups, substituted monocyclic aryl groups, polycyclic aryl groups, substituted polycyclic aryl groups, monocyclic heteroaryl groups, substituted monocyclic heteroaryl groups, polycyclic heteroaryl groups, substituted polycyclic heteroaryl groups, benzyl groups and substituted benzyl groups and combinations thereof as dimers, trimers and tetramers.

13. An electronic device comprising a semiconductor layer in contact with a number of electrodes, wherein the semiconductor layer includes at least one compound according to claim 2.

* * * * *